(12) United States Patent
Harris et al.

(10) Patent No.: US 8,343,767 B2
(45) Date of Patent: Jan. 1, 2013

(54) METHODS FOR INCREASING HOMOLOGOUS RECOMBINATION OF A NUCLEIC ACID SEQUENCES

(75) Inventors: Paul Harris, Carnation, WA (US); Howard Brody, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/434,694

(22) Filed: Mar. 29, 2012

(65) Prior Publication Data

US 2012/0231501 A1 Sep. 13, 2012

Related U.S. Application Data

(62) Division of application No. 10/420,035, filed on Apr. 21, 2003, now Pat. No. 8,148,155.

(60) Provisional application No. 60/374,639, filed on Apr. 22, 2002.

(51) Int. Cl.
*C12N 15/00* (2006.01)
*C12N 1/15* (2006.01)
*C12N 15/64* (2006.01)
*C12N 15/84* (2006.01)

(52) U.S. Cl. ....... 435/477; 435/484; 435/471; 435/69.1; 435/254.3; 435/254.4; 435/254.6; 435/254.7; 435/254.8

(58) Field of Classification Search .......... None
See application file for complete search history.

(56) References Cited

U.S. PATENT DOCUMENTS 5,989,879 A 11/1999 Reddy et al.
2004/0029129 A1 2/2004 Wang et al.

FOREIGN PATENT DOCUMENTS

| WO | 9707205 | 2/1997 |
|---|---|---|
| WO | 9932641 | 7/1999 |
| WO | 0055346 | 9/2000 |
| WO | 0214495 | 2/2002 |
| WO | 03031629 | 3/2003 |

OTHER PUBLICATIONS

Itoh et al, EMBL AB040404, downloaded Aug. 11, 2012.*
EMBL Access No. AY032591 printed Jan. 9, 2008.
Paques, F., and J. E. Haber, 1999, Microbiol. Mol. Biol. Rev. 63: 349-404, Multiple Pathways of Recombination Induced by Double-Strand Breaks in *Saccharomyces cerevisia*.
Shinohara et al., 1998, Genes Cells 3:145-56, Rad52 forms ring structures and co-operates with RPA in single-strand DNA annealing.
Osman and Subramani, 1998, Prog. Nucleic Acid Res. Mol. Biol. 58: 263-99, Double-Strand. Break-Induced i-Recombination in Eukaryote.
Bianco et al., 1998, Front Bioscience 3: d570-603, DNA Strand Exchange Proteins: A Biochemical and Physical Compartson.
Mortensen et al., 1996, Proc. Natl. Acad. Sci. USA 93: 10729-10734, DNA strand annealing is promoted by the yeast Rad52 protein.
Rattray and Symington, 1994, Genetics 138: 587-595, Use of a Chromosomal Inverted Repeat to Demonstrate That the RAD51 and RAD52 Genes of *Saccharomvces cerevisiae* Have Different Roles in Mitotic Recombination.
Bartsch et al., 2000, Mol. Cell. Biol. 20: 1194-1205, RAD51 is Required for the Repair of Plasmid Double-Stranded DNA Gaps from Either Plasmid or Chromosomal Template.
D. Van Heemst et al., Cloning, sequencing, disruption and phenotypic analysis of uvsC, an *Aspergillus nidulans* homologue of yeast RAD51, Mol. Gen. Genet., 1997 v. 254, pp. 654-664.
Holt et al., A novel phage replacement Cre-lox vector that has automatic subcloning capabilities., Gene, v. 133, 1993, pp. 95-97.
Shibayama et al., Suppression of tandem-multimer formation during genetic transformation of the mycotoxin-producing fungus *Penicillium paxilli* by disrupting an orthologue of *Aspergillus nidulans* uvsC, Curr. Genet., 2002, v. 42, pp. 59-65.
New et al., Rad52 protein stimulates DNA strand exchange by Rad51 and replication proteinA, Nature, V. 391, Jan. 22, 1998, pp. 407-410.
Benson et al., Synergistic actions of Rad51 and Rad52 in recombination and DNA repair, Nature, v. 391, Jan. 22, 1998, pp. 401-404.
UNIPROT Accession No. Q9P978, submitted in parent Apr. 26, 2006.
Guo, 2004, Proc Natl Aca Sci USA 101(25), 9205-9210, Protein tolerance to random amino acid change.
Liu, 2002, Biochem Biophys Res Comm 297, 1191-1196, Association of human RAD52 protein with transcription factors.
Lesk et al, Abst, 27-28, Prediction of Protein Function from Protein Sequence and Structure, p. 27 and 28, downloaded Sep. 16, 2007.
Singleton, 2002, Proc Natl Acad Sci USA 99(21), 13492-13497, Structure of the single-strand annealing domain of human RAD52 protein.
Smith, 1996, Protein Science 5, 2009-2019, Surface point mutations that significantly alter the structure and stability of a protein's denatured state.
Tertiary structures 2005, 1-3.
Tsukamoto, 2003, Genetics 165, 1703-1715, The N-Terminal DNA—Binding Domain of Rad52 Promotes RAD51—Independent Recombination in *Saccharomyces cerevisia*.

(Continued)

*Primary Examiner* — Maria Marvich
(74) *Attorney, Agent, or Firm* — Robert L. Starnes

(57) ABSTRACT

The present invention relates to methods for increasing homologous recombination of a nucleic acid sequence introduced into a host cell, comprising: (a) introducing into a population of filamentous fungal host cells a first nucleic acid sequence encoding a recombination protein and a second nucleic acid sequence comprising one or more regions which are homologous with the genome of the filamentous fungal host cell, wherein (i) the recombination protein promotes the recombination of the one or more regions with the corresponding homologous region in the host's genome to incorporate the second nucleic acid sequence by homologous recombination, and (ii) the number of host cells comprising the incorporated second nucleic acid sequence in the population is increased at least 20% compared to the same population without the first nucleic acid sequence; (b) and isolating from the population a filamentous fungal cell comprising the incorporated second nucleic acid sequence.

9 Claims, 14 Drawing Sheets

OTHER PUBLICATIONS

Wikipedia 2005, Prot Struc Prediction, 1-3.
Tseng, 2005, p. 1-2, Evolutionary model for predicting protein function by matching local surfaces: a Bayesian Monte Carlo approach.
EMBL Access No. AY032591, printed Jan. 9, 2008.
Kagawa et al., 2002, Molecular Cell 10, 359-371.
EMBL Access No. X75086, printed Jan. 9, 2008.
EMBL Access No. X72220, printed Jan. 9, 2008.
UNIPROTKB Accession No. P43351, printed Jan. 9, 2008.
Symington et al., 2002, Micobiol Mol Biol Revs 66(4), 630-670, Role of RAD52 Epistasis Group Genes in Homologous Recombination and Double-Strand Break Repair.
Nickoloff, J. A., and M. F. Hoekstra, 1998, Double-strand break and recombinational repair in *Saccharomyces cerevisiae*, p. 335-362.
Yanez et al., Gene targeting is enhanced in humban cells overexposing hRAD51, Gene Therapy, 1999, vol. 6, pp. 1282-1290.
Shcherbakova et al., Overexpression of bacterial RecA protein stimulates homologous recombination in somatic mammalian cells, Mutation Research, 2000, vol. 459, pp. 65-71.
Rong et al., Gene targeting by homologous recombination in Drosophila, Science, 2000, vol. 288, pp. 2013-2018.
Database EMBL Accession No. AB040404, downloaded Aug. 7, 2005.

* cited by examiner

METHODS FOR INCREASING HOMOLOGOUS RECOMBINATION OF A NUCLEIC ACID SEQUENCES

CROSS-REFERENCE TO RELATED APPLICATIONS

This application is a divisional of U.S. application Ser. No. 10/420,035, filed on Apr. 21, 2003, now U.S. Pat. No. 8,148,155, which claims the benefit of U.S. Provisional Application No. 60/374,639, filed on Apr. 22, 2002, which applications are incorporated herein by reference.

BACKGROUND OF THE INVENTION

1. Field of the Invention

The present invention relates to methods for increasing homologous recombination of a nucleic acid sequence in a filamentous fungus. The present invention also relates to isolated nucleic acid sequences encoding recombination proteins and to nucleic acid constructs, vectors, and fungal host cells comprising such nucleic acid sequences.

2. Description of the Related Art

The process of genetic engineering relies largely upon the ability of organisms to take up exogenous DNA and integrate it into their genome. Studies in model organisms have demonstrated that the integration step is a function of cellular DNA repair pathways that normally operate to maintain genomic integrity in response to DNA damage that occurs both spontaneously and as a result of exposure to a variety of exogenous agents such as ionizing radiation, ultraviolet light, and chemical mutagens (see, Nickoloff, J. A., and M. F. Hoekstra, 1998, Double-strand break and recombinational repair in *Saccharomyces cerevisiae*, p. 335-362. In J. A. Nickoloff, and M. F. Hoekstra (ed.), *DNA Damage and Repair*, Vol. I: DNA repair in prokaryotes and lower eukaryotes. Humana Press, Totowa, N.J.; Paques, F., and J. E. Haber, 1999, *Microbiol. Mol. Biol. Rev.* 63: 349-404; Shinohara et al., 1998, *Genes Cells* 3:145-56).

Integration of exogenous DNA occurs primarily through one of two major repair pathways, (1) non-homologous end joining or (2) homologous recombination. Non-homologous end joining is the direct rejoining of broken DNA ends that share little or no homology. The ends frequently require nuclease-processing before they can be ligated together, and thus non-homologous end joining is often error-prone. In contrast, homologous recombination utilizes an undamaged DNA molecule as a template to repair DNA damage in another molecule that shares homology with the undamaged one. This process is more likely to be error-free than non-homologous end joining. Techniques in genetic engineering such as gene replacement or disruption and site-specific integration rely upon homologous recombination. By manipulating the relative contribution of homologous recombination versus non-homologous end joining to overall genome repair, it should be possible to gain additional control over whether integration of exogenous DNA occurs in regions of homology versus more randomly.

In the yeast *Saccharomyces cerevisiae*, the RAD52 epistasis group includes genes that function in meiotic and mitotic homologous recombination (Nickoloff and Hoekstra, 1998, In J. A. Nickoloff, and M. F. Hoekstra (ed.), DNA Damage and Repair, Vol. I: DNA repair in prokaryotes and lower eukaryotes, p. 335-362, Humana Press, Totowa, N.J.; Osman and Subramani, 1998, *Prog. Nucleic Acid Res. Mol. Biol.* 58: 263-99; Paques and Haber, 1999, supra). Two critical genes in the homologous recombination pathway are RAD51 and RAD52. The Rad51 protein forms a stoichiometric nucleoprotein complex and, as judged by in vitro assays, mediates DNA pairing and full, stable strand exchange between single-stranded DNA and homologous duplex DNA (Bianco et al., 1998, *Front Bioscience* 3: d570-603). The Rad52 protein binds preferentially to single-stranded DNA, particularly at ends, and promotes annealing between complementary single strands (Mortensen et al., 1996, *Proc. Natl. Acad. Sci. USA* 93: 10729-10734). In *Saccharomyces cerevisiae*, RAD52 is required for all known forms of both spontaneous and induced mitotic homologous recombination. For example, intrachromosomal inverted repeat recombination is reduced 3000-fold in rad52 (Rattray and Symington, 1994, *Genetics* 138: 587-595), and plasmid gap repair by homologous recombination is essentially eliminated (Bartsch et al., 2000, *Mol. Cell. Biol.* 20: 1194-1205).

There is a need in the art for identifying and isolating recombination protein encoded genes from filamentous fungi for use in promoting interplasmid, plasmid-chromosomal, intra-chromosomal, and interchromosomal homologous recombination.

It is an object of the present invention to provide improved methods for increasing the homologous recombination of a nucleic acid sequence introduced into filamentous fungal cells.

SUMMARY OF THE INVENTION

The present invention relates to methods for increasing the homologous recombination of a nucleic acid sequence introduced into a filamentous fungal host cell, comprising: (a) introducing into a population of filamentous fungal host cells a first nucleic acid sequence encoding a recombination protein and a second nucleic acid sequence comprising one or more regions which are homologous with the genome of the filamentous fungal host cell, wherein (i) the recombination protein promotes the recombination of the one or more regions with the corresponding homologous region in the genome of the filamentous fungal host cell to incorporate the second nucleic acid sequence therein by homologous recombination, and (ii) the number of host cells comprising the incorporated second nucleic acid sequence in the population of the filamentous fungal host cells is increased at least 20% compared to the same population of filamentous fungal host cells without the first nucleic acid sequence; (b) and isolating from the population of the filamentous fungal host cells a filamentous fungal cell comprising the incorporated second nucleic acid sequence.

The present invention also relates to methods for producing a polypeptide in a filamentous fungal cell, comprising: (A) cultivating the filamentous fungal cell in a medium suitable for production of the polypeptide, wherein the filamentous fungal cell was obtained by (a) introducing into a population of filamentous fungal host cells a first nucleic acid sequence encoding a recombination protein and a second nucleic acid sequence comprising one or more regions which are homologous with the genome of the filamentous fungal host cell, wherein (i) the recombination protein promotes the recombination of the one or more regions with the corresponding homologous region in the genome of the filamentous fungal host cell to incorporate the second nucleic acid sequence therein by homologous recombination, and (ii) the number of host cells comprising the incorporated second nucleic acid sequence in the population of the filamentous fungal host cells is increased at least 20% compared to the same population of filamentous fungal host cells without the first nucleic acid sequence; and (b) isolating from the population of filamentous fungal host cells a filamentous fungal cell comprising the incorporated first nucleic acid sequence; and (B) recovering the polypeptide from the cultivation medium.

The present invention also relates to methods for deleting or disrupting a gene in a filamentous fungal cell, comprising: (a) introducing into a population of filamentous fungal host cells a first nucleic acid sequence encoding a recombination protein and a second nucleic acid sequence comprising one or more regions which are homologous with the gene of the filamentous fungal host cell, wherein (i) the recombination protein promotes the recombination of the one or more regions with the corresponding homologous region in the genome of the filamentous fungal host cell to incorporate the second nucleic acid sequence therein by homologous recombination to delete or disrupt the gene in the filamentous fungal cell, and (ii) the number of host cells comprising the incorporated second nucleic acid sequence in the population of the filamentous fungal host cells is increased at least 20% compared to the same population of filamentous fungal host cells without the first nucleic acid; and (b) isolating from the population of filamentous fungal cells a filamentous fungal cell comprising the deleted or disrupted gene.

The present invention also relates to nucleic acid sequences encoding a recombination protein selected from the group consisting of: (a) a nucleic acid sequence encoding SEQ ID NO:2, or having at least 70% identity with SEQ ID NO:4 or SEQ ID NO:6; (b) a nucleic acid sequence comprising SEQ ID NO:1, or having at least 70% homology with SEQ ID NO:3 or SEQ ID NO:5; (c) a nucleic acid sequence which hybridizes under medium stringency conditions with (i) SEQ ID NO:3 or SEQ ID NO:5, (ii) the cDNA sequence contained in SEQ ID NO:3 or SEQ ID NO:5, or (iii) a complementary strand of (i) or (ii); (d) an allelic variant of (a), (b), or (c); and (e) a subsequence of (a), (b), (c), or (d), wherein the subsequence encodes a polypeptide fragment which has recombination activity.

The present invention further relates to isolated recombination proteins encoded by such nucleic acid sequences and to nucleic acid constructs, vectors, and fungal host cells comprising the nucleic acid sequences encoding recombination proteins.

BRIEF DESCRIPTION OF THE FIGURES

FIGS. 1A and B show the genomic DNA sequence and the deduced amino acid sequence of an *Aspergillus oryzae* rdhA gene and encoded recombination protein (SEQ ID NOS:1 and 2, respectively).

Figure 3A:
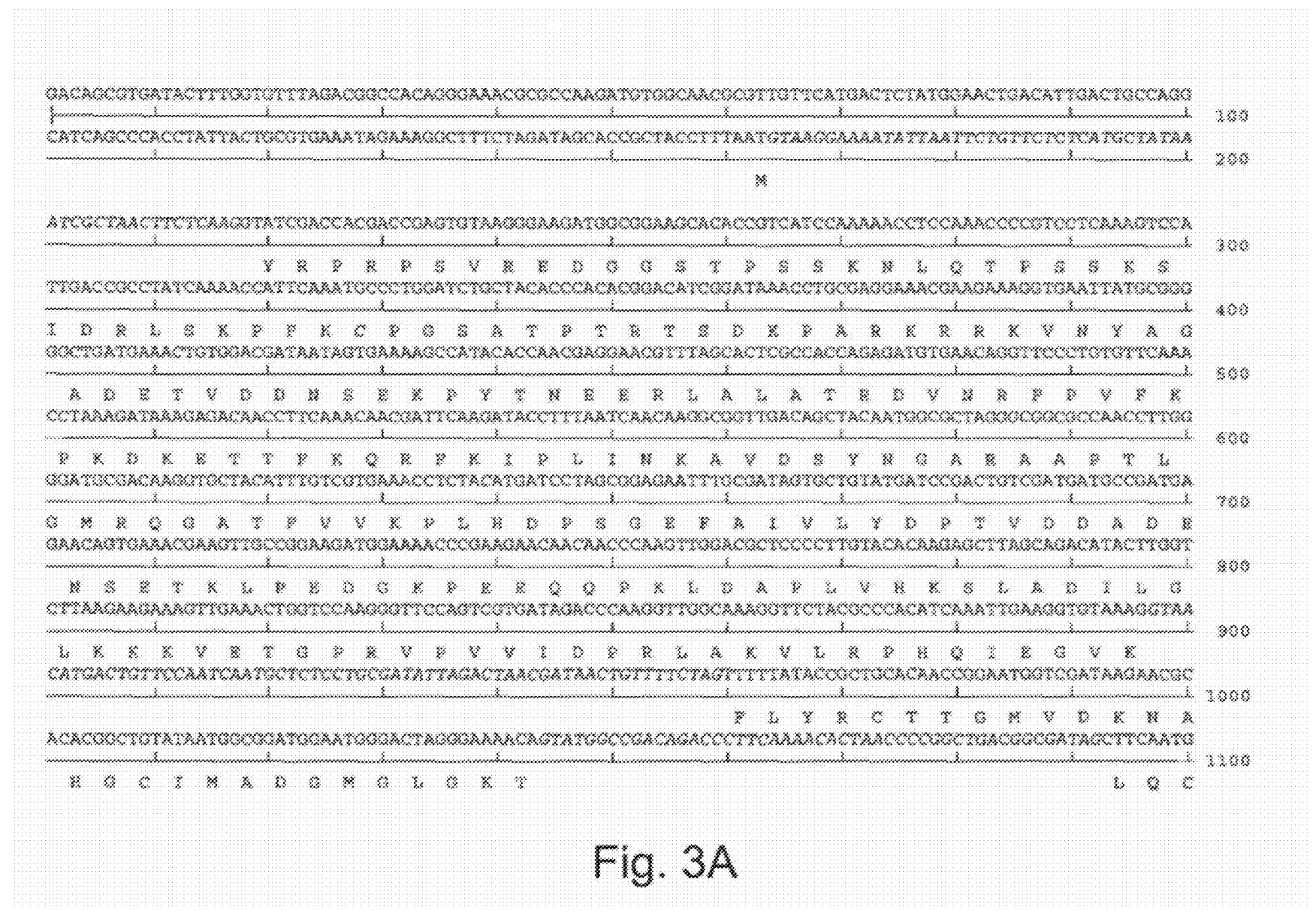
Figure 3B:
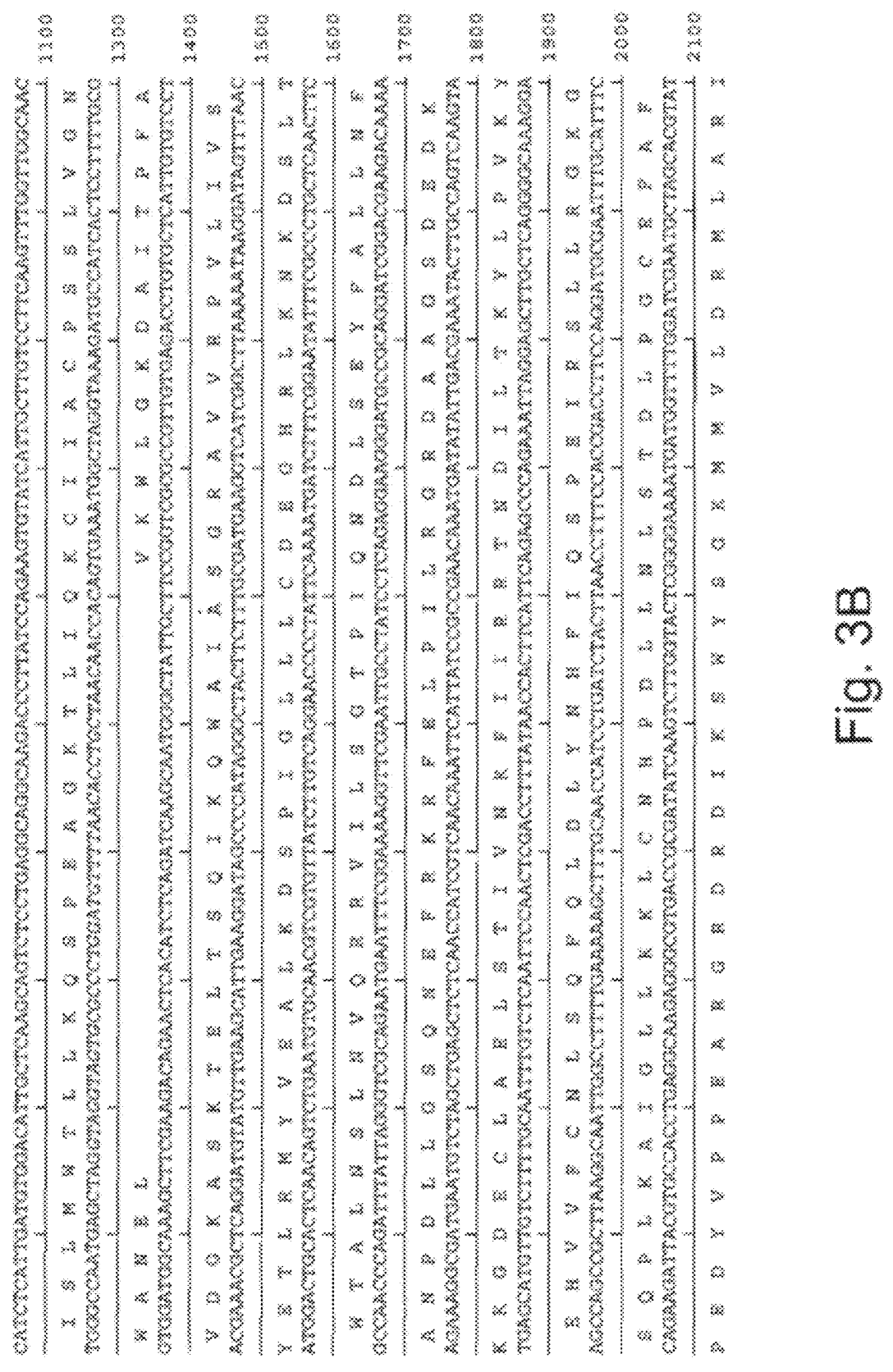
Figure 3C:
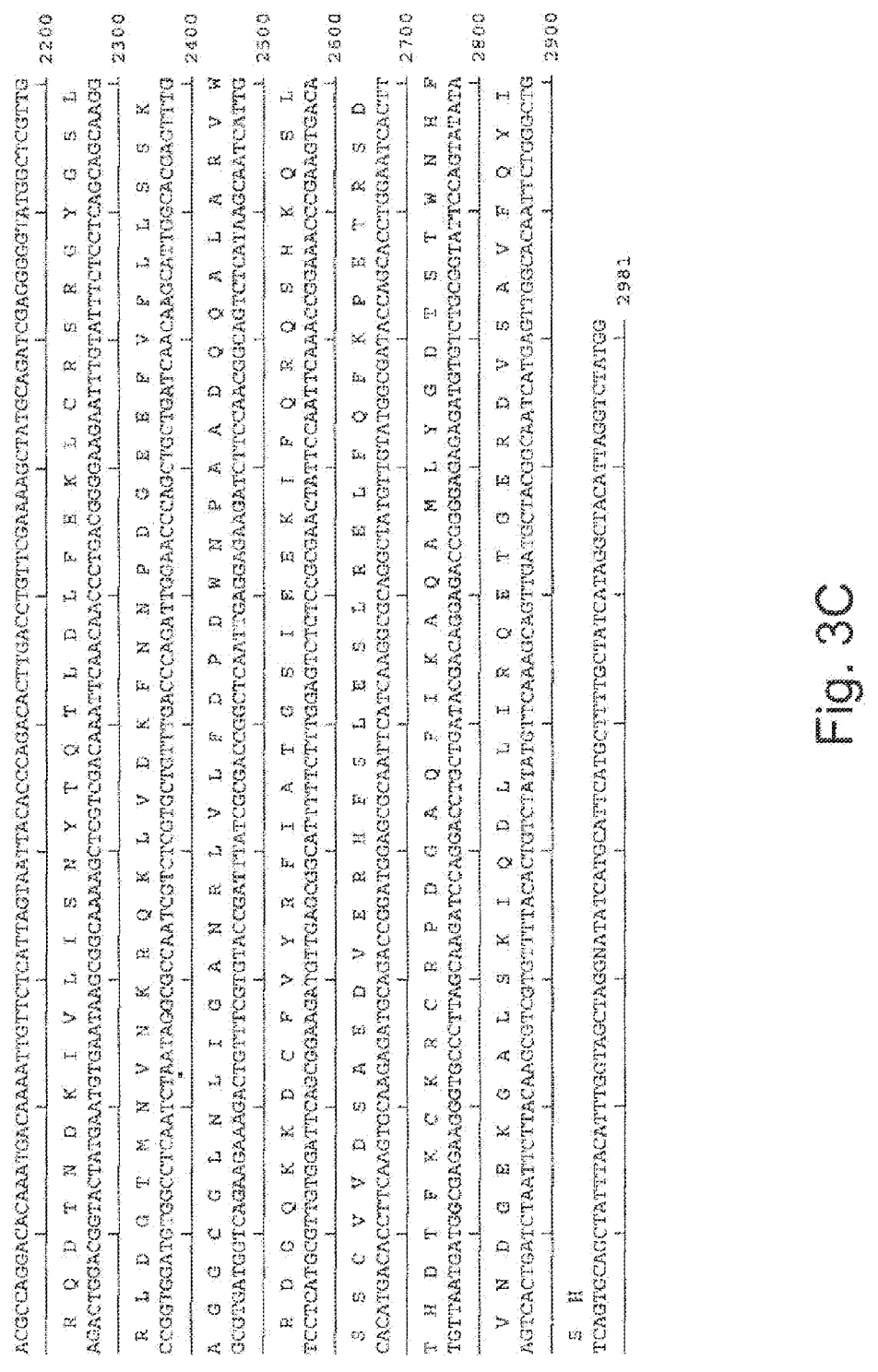

FIGS. 3A, B, and C show the genomic DNA sequence and the deduced amino acid sequence of an *Aspergillus oryzae* rdhD gene and encoded recombination protein (SEQ ID NOS:5 and 6, respectively).

DETAILED DESCRIPTION OF THE INVENTION

Figure 2A:
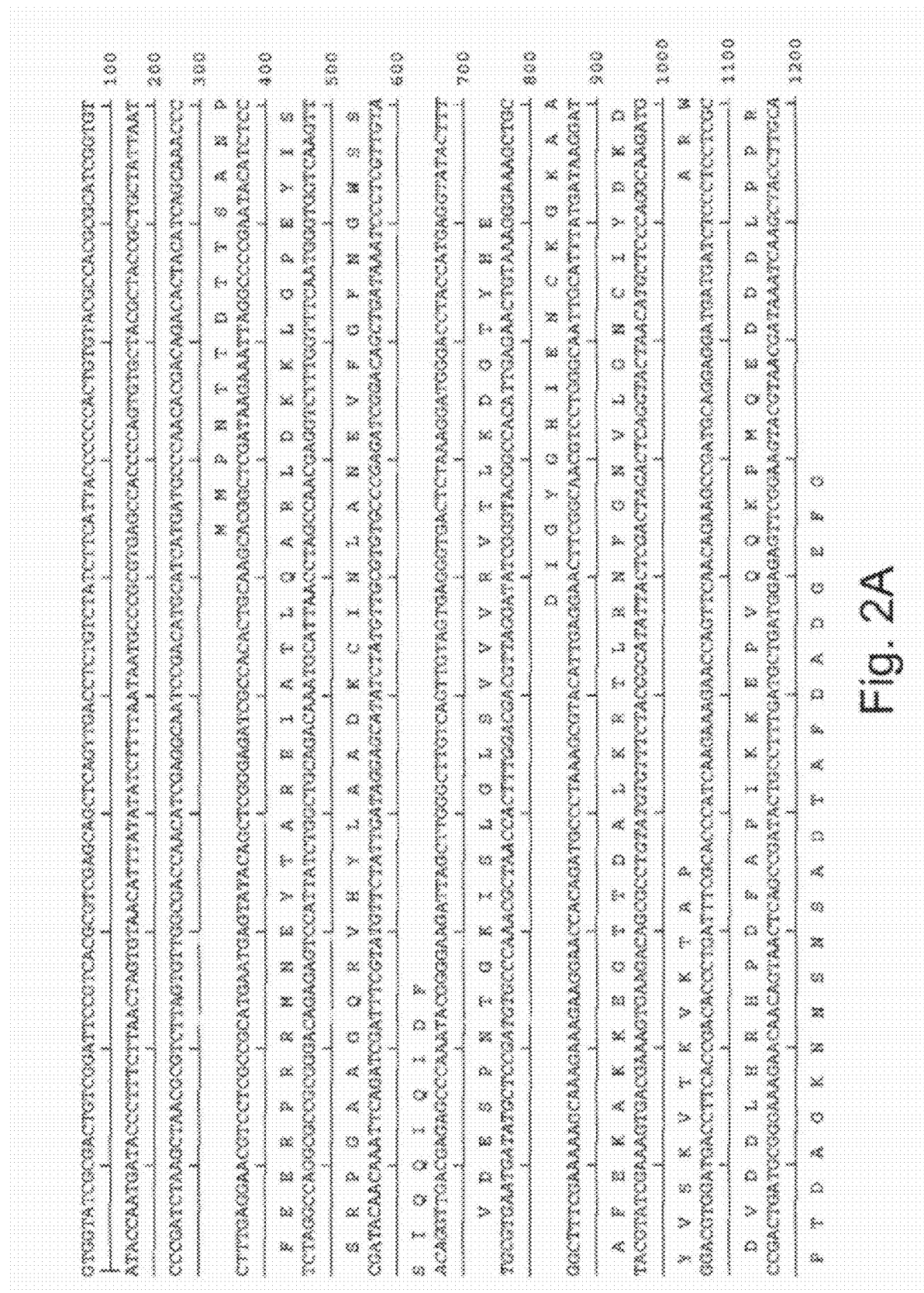
FIGS. 2A, B, and C show the genomic DNA sequence and the deduced amino acid sequence of an *Aspergillus oryzae* rdhB gene and encoded recombination protein (SEQ ID NOS:3 and 4, respectively).

The present invention relates to methods for increasing the homologous recombination of a nucleic acid sequence introduced into a filamentous fungal host cell, comprising: (a) introducing into a population of filamentous fungal host cells a first nucleic acid sequence encoding a recombination protein and a second nucleic acid sequence comprising one or more regions which are homologous with the genome of the filamentous fungal host cell, wherein (i) the recombination protein promotes the recombination of the one or more regions with the corresponding homologous region in the genome of the filamentous fungal host cell to incorporate the second nucleic acid sequence therein by homologous recombination, and (ii) the number of host cells comprising the incorporated second nucleic acid sequence in the population of the filamentous fungal host cells is increased at least 20% compared to the same population of filamentous fungal host cells without the first nucleic acid sequence; (b) and isolating from the population of the filamentous fungal host cells a filamentous fungal cell comprising the incorporated second nucleic acid sequence.

The methods of the present invention can advantageously elevate levels of homologous recombination by more than an order of magnitude, particularly by overexpressing genes encoding recombination proteins. For example, genetic engineering in *Aspergillus oryzae* and many other filamentous fungi is impeded by their asexuality and the difficulty in creating gene disruptions and other targeted integrations. The present methods overcome this difficulty.

In the methods of the present invention, the first nucleic acid sequence encoding the recombination protein may be any isolated nucleic acid sequence encoding a recombination protein.

The term "recombination protein" is defined herein as a protein that participates in the process of homologous recombination. Representative examples from *Saccharomyces cerevisiae* are Mre11, Rad50, Xrs2, RPA, Rad51, Rad52, Rad54, Rad55, Rad57, and Rad59.

The term "homologous recombination" is defined herein as the process wherein nucleic acids associate with each other in regions of homology, leading to recombination between those sequences. For purposes of the present invention, homologous recombination is determined according to the procedures summarized by Paques and Haber, 1999, *Microbiology and Molecular Biology Reviews* 63: 349-404.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The term "genome" will be understood to encompass the chromosome(s) and all extrachromosomal elements, e.g., plasmids such as autonomously replicating plasmids of a cell.

In a first embodiment, the present invention relates to isolated nucleic acid sequences encoding recombination proteins having an amino acid sequence which have a degree of identity to SEQ ID NO:2, SEQ ID NO:4 or SEQ ID NO:6 of at least about 70%, preferably at least about 75%, preferably at least about 80%, more preferably at least about 85%, even more preferably at least about 90%, most preferably at least about 95%, and even most preferably at least about 97% (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from SEQ ID NO:2, SEQ ID NO:4 or SEQ ID NO:6. For purposes of the present invention, the degree of identity between two amino acid sequences is determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple =1, gap penalty =3, windows =5, and diagonals =5.

Preferably, the nucleic acid sequences encoding recombination proteins comprise the amino acid sequence of SEQ ID NO:2, SEQ ID NO:4 or SEQ ID NO:6; or an allelic variant thereof; or a fragment thereof that has recombination activity. In a more preferred embodiment, the nucleic acid sequence encoding a recombination protein comprises the amino acid sequence of SEQ ID NO:2, SEQ ID NO:4 or SEQ ID NO:6. In another preferred embodiment, the nucleic acid sequence encoding a recombination protein consists of the amino acid sequence of SEQ ID NO:2, SEQ ID NO:4 or SEQ ID NO:6; or an allelic variant thereof; or a fragment thereof, wherein the recombination protein fragment has recombination activity.

The present invention also encompasses nucleic acid sequences which encode a recombination protein having the amino acid sequence of SEQ ID NO:2, SEQ ID NO:4 or SEQ ID NO:6, which differ from SEQ ID NO:1, SEQ ID NO:3 or SEQ ID NO:5, respectively, by virtue of the degeneracy of the genetic code. The present invention also relates to subsequences of SEQ ID NO:1, SEQ ID NO:3 or SEQ ID NO:5 which encode fragments of SEQ ID NO:2, SEQ ID NO:4 or SEQ ID NO:6, which have recombination activity.

A subsequence of SEQ ID NO:1, SEQ ID NO:3 or SEQ ID NO:5 is a nucleic acid sequence encompassed by SEQ ID NO:1, SEQ ID NO:3 or SEQ ID NO:5 except that one or more nucleotides from the 5' and/or 3' end have been deleted. Preferably, a subsequence of SEQ ID NO:1 contains at least 900 nucleotides, more preferably at least 945 nucleotides, and most preferably at least 990 nucleotides. Preferably, a subsequence of SEQ ID NO:3 contains at least 1500 nucleotides, more preferably at least 1560 nucleotides, and most preferably at least 1620 nucleotides. Preferably, a subsequence of SEQ ID NO:5 contains at least 2160 nucleotides, more preferably at least 2250 nucleotides, and most preferably at least 2350 nucleotides.

A fragment of SEQ ID NO:2, SEQ ID NO:4 or SEQ ID NO:6 is a protein having one or more amino acids deleted from the amino and/or carboxy terminus of this amino acid sequence. Preferably, a fragment of SEQ ID NO:2 contains at least 300 amino acid residues, more preferably at least 315 amino acid residues, and most preferably at least 330 amino acid residues. Preferably, a fragment of SEQ ID NO:4 contains at least 500 amino acid residues, more preferably at least 520 amino acid residues, and most preferably at least 540 amino acid residues. Preferably, a fragment of SEQ ID NO:6 contains at least 720 amino acid residues, more preferably at least 750 amino acid residues, and most preferably at least 780 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded recombination protein) or may encode recombination proteins having altered amino acid sequences. The allelic variant of a recombination protein is a recombination protein encoded by an allelic variant of a gene.

In a second embodiment, the present invention relates to isolated nucleic acid sequences which have a degree of homology to the recombination protein coding sequence of SEQ ID NO:1, SEQ ID NO:3 or SEQ ID NO:5 of at least about 70%, preferably about 75%, preferably about 80%, more preferably about 85%, even more preferably about 90%, most preferably about 95%, and even most preferably about 97% homology, which encode an active recombination protein; or allelic variants and subsequences of SEQ ID NO:1, SEQ ID NO:3 or SEQ ID NO:5 which encode recombination protein fragments which have recombination activity. For purposes of the present invention, the degree of homology between two nucleic acid sequences is determined by the Wilbur-Lipman method (Wilbur and Lipman, 1983, Proceedings of the National Academy of Science USA 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a third embodiment, the present invention relates to isolated nucleic acid sequences encoding recombination proteins having recombination activity which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) SEQ ID NO:1, SEQ ID NO:3 or SEQ ID NO:5, (ii) the cDNA sequence contained in SEQ ID NO:1, SEQ ID NO:3 or SEQ ID NO:5, (iii) a subsequence of (i) or (ii), or a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1, SEQ ID NO:3 or SEQ ID NO:5 may be at least 100 contiguous nucleotides or preferably at least 200 contiguous nucleotides. Moreover, the subsequence may encode a recombination protein fragment, which has recombination activity.

The nucleic acid sequence of SEQ ID NO:1, SEQ ID NO:3 or SEQ ID NO:5 or a subsequence thereof, as well as the amino acid sequence of SEQ ID NO:2, SEQ ID NO:4 or SEQ ID NO:6, or a fragment thereof, may be used to design a nucleic acid probe to identify and clone DNA encoding recombination proteins having recombination activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA, which hybridizes with the probes described above and which encodes a recombination protein having recombination activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, SEQ ID NO:3 or SEQ ID NO:5; or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, SEQ ID NO:3 or SEQ ID NO:5, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the recombination protein of SEQ ID NO:2, SEQ ID NO:4 or SEQ ID NO:6; or a subsequence thereof. In another preferred embodiment, the nucleic acid probe is SEQ ID NO:1, SEQ ID NO:3 or SEQ ID NO:5. In another preferred embodiment, the probe is the nucleic acid sequence encoding a recombination protein contained in plasmid pZL1rdhA13 that is contained in *Escherichia coli* NRRL B-30503. In another preferred embodiment, the probe is the nucleic acid sequence encoding the recombination protein contained in plasmid pZL1rdhB6 that is contained in *Escherichia coli* NRRL B-30503. In another preferred embodiment, the probe is the nucleic acid sequence encoding a recombination protein contained in plasmid pZL1rdhD17 that is contained in *Escherichia coli* NRRL B-30505. In another preferred embodiment, the probe is the nucleic acid sequence encoding a recombination protein contained in plasmid pZL1rdhD10 that is contained in *Escherichia coli* NRRL B-30506.

For long probes of at least 100 nucleotides in length, very low to very high stringency conditions are defined as prehybridization and hybridization at 42° C. in 5× SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2× SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6× SCC plus 0.1% SDS for 15 minutes and twice each for 15 minutes using 6× SSC at 5° C. to 10° C. below the calculated $T_m$.

The present invention also relates to isolated nucleic acid sequences produced by (a) hybridizing a DNA under very low, low, medium, medium-high, high, or very high stringency conditions with (i) SEQ ID NO:1, SEQ ID NO:3 or SEQ ID NO:5; (ii) the cDNA sequence contained in nucleotides SEQ ID NO:1, SEQ ID NO:3 or SEQ ID NO:5; (iii) a subsequence of (i) or (ii); or (iv) a complementary strand of (i), (ii), or (iii); and (b) isolating the nucleic acid sequence. The subsequence is preferably a sequence of at least 100 contiguous nucleotides such as a sequence, which encodes a recombination protein fragment which has recombination activity.

In a fourth embodiment, the present invention relates to isolated nucleic acid sequences which encode variants of the recombination protein having an amino acid sequence of SEQ ID NO:2, SEQ ID NO:4 or SEQ ID NO:6, comprising a substitution, deletion, and/or insertion of one or more amino acids.

The amino acid sequences of the variant recombination proteins may differ from the amino acid sequence of SEQ ID NO:2, SEQ ID NO:4 or SEQ ID NO:6, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Modification of a nucleic acid sequence of the present invention may be necessary for the synthesis of recombination proteins substantially similar to the recombination protein. The term "substantially similar" to the recombination protein refers to non-naturally occurring forms of the recombination protein. These recombination proteins may differ in some engineered way from the recombination protein isolated from its native source, e.g., variants that differ in specific activity, thermostability, pH optimum, or the like. The variant sequence may be constructed on the basis of the nucleic acid sequence presented as the recombination protein encoding part of SEQ ID NO:1, SEQ ID NO:3 or SEQ ID NO:5, e.g., a subsequence thereof, and/or by introduction of nucleotide substitutions which do not give rise to another amino acid sequence of the recombination protein encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active recombination protein. Amino acid residues essential to the activity of the recombination protein encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for recombination activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The nucleic acid sequences encoding recombination proteins may be obtained from microorganisms of any genus. For purposes of the present invention, the term "obtained from" as used herein in connection with a given source shall mean that the recombination protein encoded by the nucleic acid sequence is produced by the source or by a cell in which the nucleic acid sequence from the source has been inserted.

The nucleic acid sequences encoding recombination proteins may be obtained from any filamentous fungal source including, but not limited to, an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* strain.

In a preferred embodiment, the nucleic acid sequences are obtained from a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

In another preferred embodiment, the nucleic acid sequences are obtained from an *Aspergillus aculeatus, Aspergillus awamori, Aspergillus foetidus, Aspergillus japonicus, Aspergillus nidulans, Aspergillus niger,* or *Aspergillus oryzae* strain.

In a more preferred embodiment, the nucleic acid sequences are obtained from *Aspergillus oryzae*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

In a most preferred embodiment, the nucleic acid sequence encoding the recombination protein is set forth in SEQ ID NO:1. In another most preferred embodiment, the nucleic acid sequence is the sequence contained in plasmid pZL1rdhA13 that is contained in *Escherichia coli* NRRL B-30503. In another most preferred embodiment, the nucleic acid sequence is set forth in SEQ ID NO:3. In another most preferred embodiment, the nucleic acid sequence encoding the recombination protein is the sequence contained in plasmid pZL1rdhB6 that is contained in *Escherichia coli* NRRL B-30503. In another most preferred embodiment, the nucleic acid sequence encoding the recombination protein is set forth in SEQ ID NO:5. In another most preferred embodiment, the nucleic acid sequence is the sequence contained in plasmid pZL1rdhD17 that is contained in *Escherichia coli* NRRL B-30505. In another most preferred embodiment, the nucleic acid sequence encoding the recombination protein is set forth in SEQ ID NO:7. In another most preferred embodiment, the nucleic acid sequence is the sequence contained in plasmid pZL1rdhD10 that is contained in *Escherichia coli* NRRL B-30506.

The present invention also relates to mutant nucleic acid sequences comprising at least one mutation in the recombination protein coding sequence of SEQ ID NO:1, SEQ ID NO:3 or SEQ ID NO:5 in which the mutant nucleic acid sequence encodes a polypeptide which consists of SEQ ID NO:2, SEQ ID NO:4 or SEQ ID NO:6, respectively.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Aspergillus*, or another or related organism and thus, for example, may be an allelic or species variant of the polypeptide encoding region of the nucleic acid sequence.

In the methods of the present invention, the first nucleic acid sequences encoding recombination proteins are preferably overexpressed. Overexpression of these genes can be accomplished by multiple insertions of the genes in the genome of the filamentous fungal host cell and/or by substituting heterologous control sequences for the native control sequences in the gene, e.g., a strong promoter.

In the methods of the present invention, the second nucleic acid may be any nucleic acid sequence. The second nucleic acid sequence preferably comprises (a) a gene that encodes a polypeptide or an RNA; (b) a gene disrupted with a third nucleic acid sequence; (c) a partially or fully deleted gene; (d) a regulatory control sequence; or (e) a recombinantly manipulated version of a gene native or foreign to the filamentous fungal host cell.

In a preferred embodiment, the second nucleic acid sequence comprises a gene encoding a polypeptide or an RNA. The polypeptide or RNA encoded by the nucleic acid sequence may be native or heterologous to the fungal host cell of interest.

The term "polypeptide" is not meant herein to refer to a specific length of the encoded product and, therefore, encompasses peptides, oligopeptides, and proteins. The term "heterologous polypeptide" is defined herein as a polypeptide which is not native to the fungal cell, a native polypeptide in which modifications have been made to alter the native sequence, or a native polypeptide whose expression is quantitatively altered as a result of a manipulation of the fungal cell by recombinant DNA techniques. For example, a native polypeptide may be recombinantly produced by, e.g., placing a gene encoding the polypeptide under the control of a promoter sequence. The filamentous fungal cell may contain one or more copies of the nucleic acid sequence encoding the polypeptide.

Preferably, the polypeptide is an antibody, hormone, enzyme, receptor, reporter, or selectable marker. In a preferred embodiment, the polypeptide is secreted extracellularly. In a more preferred embodiment, the polypeptide is an oxidoreductase, transferase, hydrolase, lyase, isomerase, or ligase. In an even more preferred embodiment, the polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase.

The nucleic acid sequence encoding a polypeptide of interest may be obtained from any prokaryotic, eukaryotic, or other source. The techniques used to isolate or clone a nucleic acid sequence encoding a polypeptide of interest are known in the art and include isolation from genomic DNA, preparation from cDNA, or a combination thereof, as described above. The nucleic acid sequence may be of genomic, cDNA, RNA, semisynthetic, synthetic origin, or any combinations thereof.

In the methods of the present invention, the polypeptide may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the mutant fungal cell.

The selectable marker gene may be, but is not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), and trpC (anthranilate synthase); and equivalents thereof.

In another preferred embodiment, the second nucleic acid sequence comprises a disrupted gene. The gene may be disrupted with any nucleic acid sequence. In a preferred embodiment, the gene is disrupted with a selectable marker gene selected from the group described above.

In another preferred embodiment, the second nucleic acid sequence comprises a partially or fully deleted gene. Where the nucleic acid sequence comprises a fully deleted gene, it will be understood that the nucleic acid sequence will contain regions upstream and downstream of the gene that are homologous with corresponding homologous regions in the genome of the filamentous fungal cell.

The second nucleic acid sequence comprising a disrupted or deleted gene may be constructed by using methods well known in the art, for example, insertions, disruptions, replacements, or deletions. The gene to be disrupted or deleted may be, for example, the coding region or a part thereof essential for activity, or the gene may contain a regulatory element required for expression of the coding region. An example of such a regulatory or control sequence may be a promoter sequence or a functional part thereof, i.e., a part which is sufficient for affecting expression of the nucleic acid sequence. Other control sequences for possible modification include, but are not limited to, a leader, polyadenylation sequence, propeptide sequence, signal sequence, transcription terminator, and transcriptional activator.

Disruption or deletion of the gene may be also accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change of the open reading frame.

An example of a convenient way to disrupt or delete a gene is based on techniques of gene replacement, gene deletion, or gene disruption. For example, in the gene disruption method, a nucleic acid sequence corresponding to the endogenous gene or gene fragment of interest is mutagenized in vitro to produce a defective nucleic acid sequence which is then transformed into the parent cell to produce a defective gene. By homologous recombination, the defective nucleic acid sequence replaces the endogenous gene or gene fragment. It may be desirable that the defective gene or gene fragment also encodes a marker, which may be used for selection of transformants in which the nucleic acid sequence has been modified or destroyed. The selectable marker gene may be used to achieve the disruption. The defective nucleic acid sequence may be a simple disruption of the endogenous sequence with a selectable marker gene. Alternatively, the defective nucleic acid sequence may contain an insertion or deletion of the endogenous sequence, or a portion thereof, in addition to the disruption with the selectable marker gene. Furthermore, the defective nucleic acid sequence may contain an insertion or deletion of the endogenous sequence, or a portion thereof, and the selectable marker gene is not involved in the modification but is used as a selectable marker for identifying transformants containing the defective gene.

In another preferred embodiment, the second nucleic acid sequence comprises a regulatory control sequence. The regulatory control sequence can be any control sequence, including, but not limited to, a promoter, signal sequence, leader, polyadenylation sequence, propeptide sequence, consensus translational initiator sequence, signal peptide sequence, and transcription terminator.

In another preferred embodiment, the second nucleic acid sequence comprises a recombinantly manipulated version of a gene native or foreign to the filamentous fungal host cell. Further discussion of constructing a recombinantly manipulated version of a gene is discussed below.

The second nucleic acid sequence comprises one or more regions, which are homologous with the genome of the filamentous fungal host cell. The recombination protein promotes the recombination of the one or more regions with the corresponding homologous region in the genome of the filamentous fungal host cell to incorporate the second nucleic acid sequence therein by homologous recombination. In the methods of the present invention any region that is homologous with the genome of the filamentous fungal host cell may be used.

In a preferred embodiment, the one or more regions homologous with the genome of the filamentous fungal cell can be a 5' region and/or a 3' region that flank (a) a gene that encodes a polypeptide or an RNA; (b) a gene disrupted with a third nucleic acid sequence; (c) a partially gene; (d) a regulatory control sequence; or (e) a recombinantly manipulated version of a gene native or foreign to the filamentous fungal host cell.

In another preferred embodiment, the one or more regions homologous with the genome of the filamentous fungal cell can be the 5' region and/or a 3' region of (a) a gene that encodes a polypeptide or an RNA; (b) a gene disrupted with a third nucleic acid sequence; (c) a partially or fully deleted gene; (d) a regulatory control sequence; or (e) a recombinantly manipulated version of a gene native or foreign to the filamentous fungal host cell.

In another preferred embodiment, the one or more regions homologous with the genome of the filamentous fungal cell can be a part of a gene native or foreign to the filamentous fungal host cell.

In the methods of the present invention, when the second nucleic acid sequence comprises one or more contiguous regions that are homologous with the genome of the filamentous fungal cell, the second nucleic acid sequence may integrate into the genome by homologous recombination via a number of possible mechanisms, yielding a variety of recombinant nucleic acid structures. These include but are not limited to complete integration of the second nucleic acid sequence into the genome, replacement of a portion of the genome by a portion of the second nucleic acid sequence, or reciprocal exchange of a portion of the genome and a portion of the second nucleic acid sequence. (see, for example, Paques and Haber, 1999, *Microbiology and Molecular Biology Reviews* 63: 349-404).

Nucleic Acid Constructs

The present invention also relates nucleic acid constructs comprising the first nucleic acid sequence and/or the second nucleic acid sequence operably linked to one or more control sequences which direct the expression of the coding sequence in a suitable host cell under conditions compatible with the control sequences. Expression will be understood to include any step including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleic acid sequence encoding a polypeptide may be further manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

In the methods of the present invention, the nucleic acid sequence may comprise one or more native control sequences or one or more of the native control sequences may be replaced with one or more control sequences foreign to the nucleic acid sequence for improving expression of the coding sequence in a host cell.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, consensus translational initiator sequence of the present invention, signal peptide sequence, and transcription terminator. At a minimum, the control sequences include transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The control sequence may be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Rhizomucor miehei* aspartic proteinase and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of a gene encoding a polypeptide which is endogenous to a host cell. The constructs may contain the minimal number of components necessary for altering expression of the endogenous gene. In one embodiment, the nucleic acid constructs preferably contain (a) a targeting sequence, (b) an exon, and (c) a splice-donor site. Upon introduction of the nucleic acid construct into a cell, the construct inserts by homologous recombination into the cellular genome at the endogenous gene site. The targeting sequence directs the integration of elements (a)-(c) into the endogenous gene such that elements (b)-(c) are operably linked to the endogenous gene. In another embodiment, the nucleic acid constructs contain (a) a targeting sequence, (b) an exon, (c) a splice-donor site, (d) an intron, and (e) a splice-acceptor site, wherein the targeting sequence directs the integration of elements (a)-(e) such that elements (b)-(e) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5'-non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5'-of the second exon, and the splice-donor site overlapping and flanking the first exon on its 3' side recognizes a splice-acceptor site flanking the second exon on the 5'-side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising comprising the first nucleic acid sequence and/or the second nucleic acid sequence, and transcriptional and translational stop signals. The various nucleic acid and control sequences described above may be joined together to produce a recombinant expression vector which may include one or more convenient restriction sites to allow for insertion or substitution of the promoter and/or nucleic acid sequence encoding the polypeptide at such sites. Alternatively, the nucleic acid sequence may be expressed by inserting the nucleic acid sequence or a nucleic acid construct comprising the consensus translational initiator sequence and/or sequence into an appropriate vector for expression. In creating the expression vector, the coding sequence is located in the vector so that the coding sequence is operably linked with a consensus translational initiator sequence of the present invention and one or more appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaA (nitrite reuctase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the filamentous fungal host cell in question. Examples of yeast origins of replication are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of the first nucleic acid sequence and/or the second nucleic acid sequence may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

In the methods of the present invention, the first and/or second nucleic acid sequence is contained in a plasmid, an autonomously replicating plasmid, or linear DNA fragment when introduced into the filamentous fungal host cell. The first and second nucleic acid sequences may be on the same plasmid, autonomously replicating plasmid, or linear DNA fragment, or on different plasmids, an autonomously replicating plasmids, or linear DNA fragments. The first nucleic acid sequence may be introduced into the filamentous fungal host cell prior to or simultaneously with the second nucleic acid sequence.

The first and/or second nucleic acid sequences may be introduced into the chromosome or into an autonomously replicating plasmid of the filamentous fungal host cell.

Host Cells

The present invention also relates to recombinant filamentous fungal host cells, comprising a first nucleic acid sequence encoding a recombination protein, which is advantageously used in increasing the homologous recombination of a second nucleic acid sequence introduced into the filamentous fungal host cell. A vector comprising a nucleic acid sequence encoding a recombination protein is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any filamentous fungal cell useful in the methods of the present invention. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a preferred embodiment, the filamentous fungal host cell is an *Acremonium, Aspergillus, Fusarium, Humicola, Mucor, Myceliophthora, Neurospora, Penicillium, Thielavia, Tolypocladium*, or *Trichoderma* cell.

In a more preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

In a most preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787.

In most preferred embodiment, the filamentous fungal host cell, comprises a nucleic acid sequence encoding a recombination protein selected from the group consisting of: (a) a nucleic acid sequence having at least 70% identity with SEQ ID NO: 2, SEQ ID NO:4 or SEQ ID NO:6; (b) a nucleic acid sequence having at least 70% homology with SEQ ID NO:1, SEQ ID NO:3 or SEQ ID NO:5; (c) a nucleic acid sequence which hybridizes under medium stringency conditions with (i) SEQ ID NO:1, SEQ ID NO:3 or SEQ ID NO:5, (ii) the cDNA sequence contained in SEQ ID NO:1, SEQ ID NO:3 or SEQ ID NO:5, or (iii) a complementary strand of (i) or (ii); and (d) a subsequence of (a), (b), or (c), wherein the subsequence encodes a polypeptide fragment which has recombination activity.

In the methods of the present invention, the number of host cells comprising the incorporated second nucleic acid sequence in the population of the filamentous fungal host cells is increased at least 20%, preferably at least 50%, more preferably at least 100%, even more preferably at least 500%, most preferably at least 1000%, and even most preferably at least 2000% compared to the same population of filamentous fungal host cells without the first nucleic acid sequence.

Methods of Production

The present invention also relates to methods for producing a polypeptide in a filamentous fungal cell, comprising: (A) cultivating the filamentous fungal cell in a medium suitable for production of the polypeptide, wherein the filamentous fungal cell was obtained by (a) introducing into a population of filamentous fungal host cells a first nucleic acid sequence encoding a recombination protein and a second nucleic acid sequence comprising one or more regions which are homologous with the genome of the filamentous fungal host cell, wherein (i) the recombination protein promotes the recombination of the one or more regions with the corresponding homologous region in the genome of the filamentous fungal host cell to incorporate the second nucleic acid sequence therein by homologous recombination, and (ii) the number of host cells comprising the incorporated second nucleic acid sequence in the population of the filamentous fungal host cells is increased at least 20% compared to the same population of filamentous fungal host cells without the first nucleic acid sequence; and (b) isolating from the population of filamentous fungal host cells a filamentous fungal cell comprising the incorporated first nucleic acid sequence; and (B) recovering the polypeptide from the cultivation medium.

The present invention also relates to methods for producing a recombination protein of the present invention comprising (a) cultivating a host cell under conditions conducive for production of the recombination protein; and (b) recovering the polypeptide.

The present invention further relates to methods for producing a polypeptide comprising (a) cultivating a homologously recombinant filamentous fungal cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the above methods of production, the filamentous fungal cell comprises a nucleic acid sequence encoding a recombination protein selected from the group consisting of: (a) a nucleic acid sequence having at least 70% identity with SEQ ID NO: 2, SEQ ID NO:4 or SEQ ID NO:6; (b) a nucleic acid sequence having at least 70% homology with SEQ ID NO:1, SEQ ID NO:3 or SEQ ID NO:5; (c) a nucleic acid sequence which hybridizes under medium stringency conditions with (i) SEQ ID NO:1, SEQ ID NO:3 or SEQ ID NO:5, (ii) the cDNA sequence contained in SEQ ID NO:1, SEQ ID NO:3 or SEQ ID NO:5, or (iii) a complementary strand of (i) or (ii); and (d) a subsequence of (a), (b), or (c), wherein the subsequence encodes a polypeptide fragment which has recombination activity.

In the production methods of the present invention, the filamentous fungal cells are cultivated in a nutrient medium suitable for production of the polypeptide using methods known in the art. For example, the cells may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

The present invention is further described by the following examples which should not be construed as limiting the scope of the invention.

EXAMPLES

Chemicals Used as Buffers and Substrates were Commercial Products of at Least Reagent Grade.
Strains

*Aspergillus oryzae* HowB101 (A1560, pyrGΔ), *Aspergillus oryzae* HowB425, *Aspergillus oryzae* HowB430 (HowB101, lipolase::amdS), *Aspergillus oryzae* HowB443 (HowB101, TAKArdhA::basta$^R$), *Aspergillus oryzae* HowB445 (HowB101, TAKArdhB:: basta$^R$, *Aspergillus oryzae* HowB446 (HowB101, niaArdhB:: basta$^R$), *Aspergillus oryzae* SE29-70 (HowB425, hemAΔ5'::pyrG), *Aspergillus oryzae* PaHa29 (SE29-70, pyrGΔ), *Aspergillus oryzae* PaHa30 (PaHa29, TAKArdhA::pyrG), *Aspergillus oryzae* PaHa31 (PaHa29, TAKArdhB::pyrG), *Aspergillus oryzae* PaHa32 (PaHa29, niaArdhA::pyrG), *Aspergillus oryzae* PaHa33 (PaHa29, niaArdhB::pyrG), *Aspergillus oryzae* PaHa31-2.2 (PaHa31, hemAΔ3':amdS), *Aspergillus oryzae* PaHa32-4.6 (PaHa32, hemAΔ3':amdS), and *Aspergillus oryzae* PaHa33-5.1 (PaHa33, hemAΔ3'::amdS).

Example 1

*Aspergillus oryzae* Genomic DNA Extraction

*Aspergillus oryzae* HowB101, *Aspergillus oryzae* HowB430, or *Aspergillus oryzae* HowB425 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

Example 2

PCR Amplification of a Portion of the *Aspergillus oryzae* rdhA Gene

A portion of the *Aspergillus oryzae* rdhA (rad51 homolog A) gene was amplified by hemi-nested degenerate PCR. The first amplification employed degenerate primers 971514 and 971515, shown below, coding for amino acids DNVAYAR and MFNPDPK.

```
Primer 971514 (DNVAYAR):
5'-GAYAAYGTIGCITAYGCNMG-3'     (SEQ ID NO: 7)

Primer 971515 (MFNPDPK):
5'-TTIGGRTCNGGRTTRAACAT-3'     (SEQ ID NO: 8)
```

The amplification reactions (30 μl) were prepared using *Aspergillus oryzae* HB101 genomic DNA as template with the following components: PCR buffer II (Perkin Elmer, Branchburg, N.J.), 0.25 mM dNTPs, 0.8 μg of *Aspergillus oryzae* HowB101 genomic DNA, 6.4 μM primer 971514, 3.2

µM primer 971515, and 1.5 units of Taq DNA polymerase (Perkin Elmer, Branchburg, N.J.). Before amplification, the template DNA was denatured in a boiling water bath for 5 minutes and quick-cooled on ice. The reaction was initiated by adding Taq DNA polymerase to the other reaction components at 72° C. The reactions were incubated in a Perkin-Elmer Model 480 Thermal Cycler programmed as follows: 35 cycles each for 20 seconds at 94° C., 30 seconds at 66° C., 60 seconds ramping from 66 to 50° C., and 60 seconds at 72° C. (5 minute final extension). The reaction products were isolated on a 1.6% agarose gel using 40 mM Tris base-20 mM sodium acetate-1 mM disodium EDTA (TAE) buffer where a 300 bp product band was excised from the gel and purified using a QIAquick Gel Extraction Kit (QIAGEN, Chatsworth, Calif.) according to the manufacturer's instructions.

One-tenth of the isolated 300 bp product was amplified under the same conditions described above except that primer 971516, shown below, was used in place of primer 971515.

```
Primer 971516 (NQVVAQV):
5'-ACYTGIGCIACNACYTGRTT-3'     (SEQ ID NO: 9)
```

The products were fractionated as before and a band at approximately 260 bp was excised and purified as described for the 300 bp product.

The purified PCR product was subsequently subcloned using the TOPO TA Cloning kit (Invitrogen, Carlsbad, Calif.) according to the manufacturer's instructions and the DNA sequence was determined using M13 Forward (−20) Primer (Invitrogen, Carlsbad, Calif.). DNA sequence analysis of the 260 bp rdhA gene segment showed that the amplified gene segment encoded a portion of the corresponding *Aspergillus oryzae* rdhA gene.

Example 3

Isolation of a Full-Length *Aspergillus oryzae* rdhA Genomic Clones

Genomic DNA libraries were constructed using the bacteriophage cloning vector λZipLox (Life Technologies, Gaithersburg, Md.) with *E. coli* Y1090ZL cells (Life Technologies, Gaithersburg, Md.) as a host for plating and purification of recombinant bacteriophage and *E. coli* DH10Bzip (Life Technologies, Gaithersburg, Md.) for excision of individual pZL1 clones containing the rdhA gene.

*Aspergillus oryzae* HowB425 genomic DNA was partially digested with Tsp509I and size-fractionated on 1% agarose gels. DNA fragments migrating in the size range 3-7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *Escherichia coli* Y1090ZL cells (Life Technologies, Gaithersburg, Md.).

The *Aspergillus oryzae* HowB425 DNA library was plated on NZCYM agar plates. Plaque lifts (Maniatis et al., 1982, *Molecular Cloning, A Laboratory Manual*, Cold Spring Harbor Press, Cold Spring Harbor, N.Y.) were performed on approximately 40,000 pfu and the DNA was fixed onto membranes by heating at 80° C. for two hours. The membranes were soaked for 30 minutes at 65° C. in a hybridization solution containing 6× SSPE and 7.0% SDS.

The subcloned rdhA product of the PCR amplification described in Example 2 was excised from the vector pCR2.1—TOPO by digestion with EcoRI. Approximately 28 ng was random-primer labeled using a Stratagene Prime-It II Kit (Stratagene, La Jolla, Calif.) according to the manufacturer's instructions and used to probe the approximately 40,000 pfu of the *Aspergillus oryzae* genomic library constructed from *Aspergillus oryzae* strain HowB425 in the vector λZipLox. The radiolabeled rdhA gene fragment was then denatured by adding sodium hydroxide to a final concentration of 0.5 M, and added to the hybridization solution at an activity of approximately $1 \times 10^6$ cpm per ml of hybridization solution. The mixture was incubated overnight at 65° C. in a shaking water bath. Following incubation, the membranes were washed two times in 0.2× SSC with 0.2% SDS at room temperature and an additional two times in the same solution at 65° C. The membranes were then sandwiched between sheets of plastic and exposed to X-ray film for 18 hours at −80° C. with intensifying screens (Kodak, Rochester, N.Y.).

Fourteen plaques produced strong hybridization signals with the probe. Twelve of the plaques were picked from the plates and eluted overnight in 1 ml of SM (5.8 g/l NaCl, 2 g/l $MgSO_4 \cdot 7H_2O$, 50 mM Tris-Cl, 0.01% gelatin). For plaque purification, the eluates were diluted 1:100 and 2 µl of the dilution was plated on NZCYM plates together with Y1090ZL plating bacteria. Plaque lifts were prepared and screened as described above, and individual plaques were picked into 0.5 ml of SM. The pZL1 plasmids were excised from the purified phagemid clones according to the protocol suggested by Life Technologies (Gaithersburg, Md.). Colonies were inoculated into three ml of LB plus 50 µg/ml ampicillin medium and grown overnight at 37° C. Miniprep DNA was prepared from each of these clones using the Qiagen Bio Robot 9600 according to the manufacturer's protocol. The plasmids were digested with EcoRI and XbaI and fractionated by agarose gel electrophoresis in order to determine if the clones were identical and to determine their sizes. The nine unique clones had insert sizes ranging from 3.15 to 6.4 kb.

Example 4

Characterization of the *Aspergillus oryzae* Genomic Clone Encoding RDHA

DNA sequencing of each clone was performed with an Applied Biosystems Prism 377 DNA Sequencer using the BigDye Terminator Cycle Sequencing Ready Reaction kit (ABI, Foster City, Calif.) according to the manufacturer's instructions. Oligonucleotide sequencing primers were designed to complementary sequences in the pZL1 plasmid vector and were synthesized by Operon Technologies Inc., Alameda, Calif. Contig sequences were generated by sequencing from the ends of each pZL1 clone and by sequencing subclones obtained from SalI, PstI, or HindIII digests of Clone #3, Clone #7, Clone #12, or Clone 13.

Figure 1A:
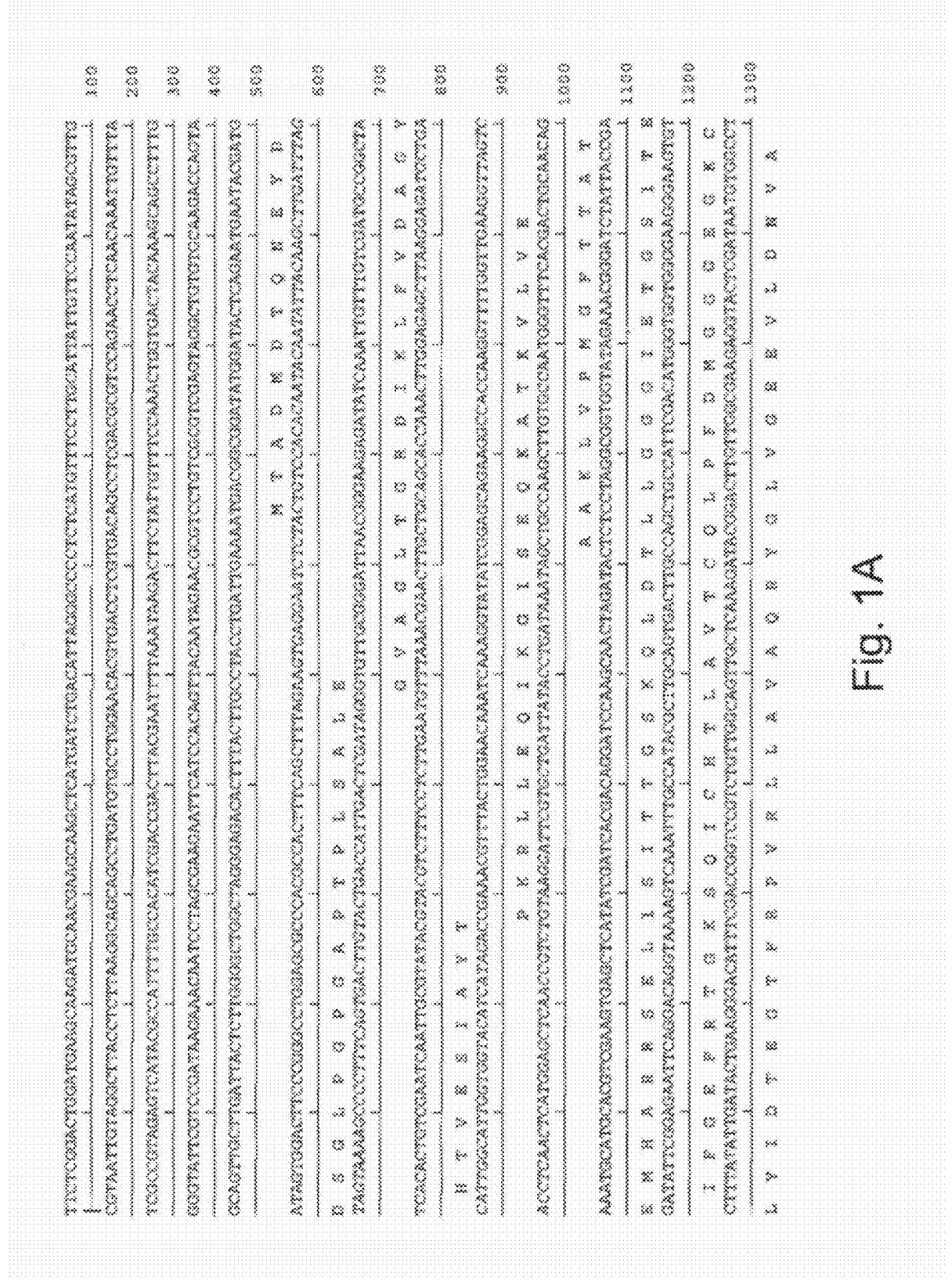
Figure 1B:
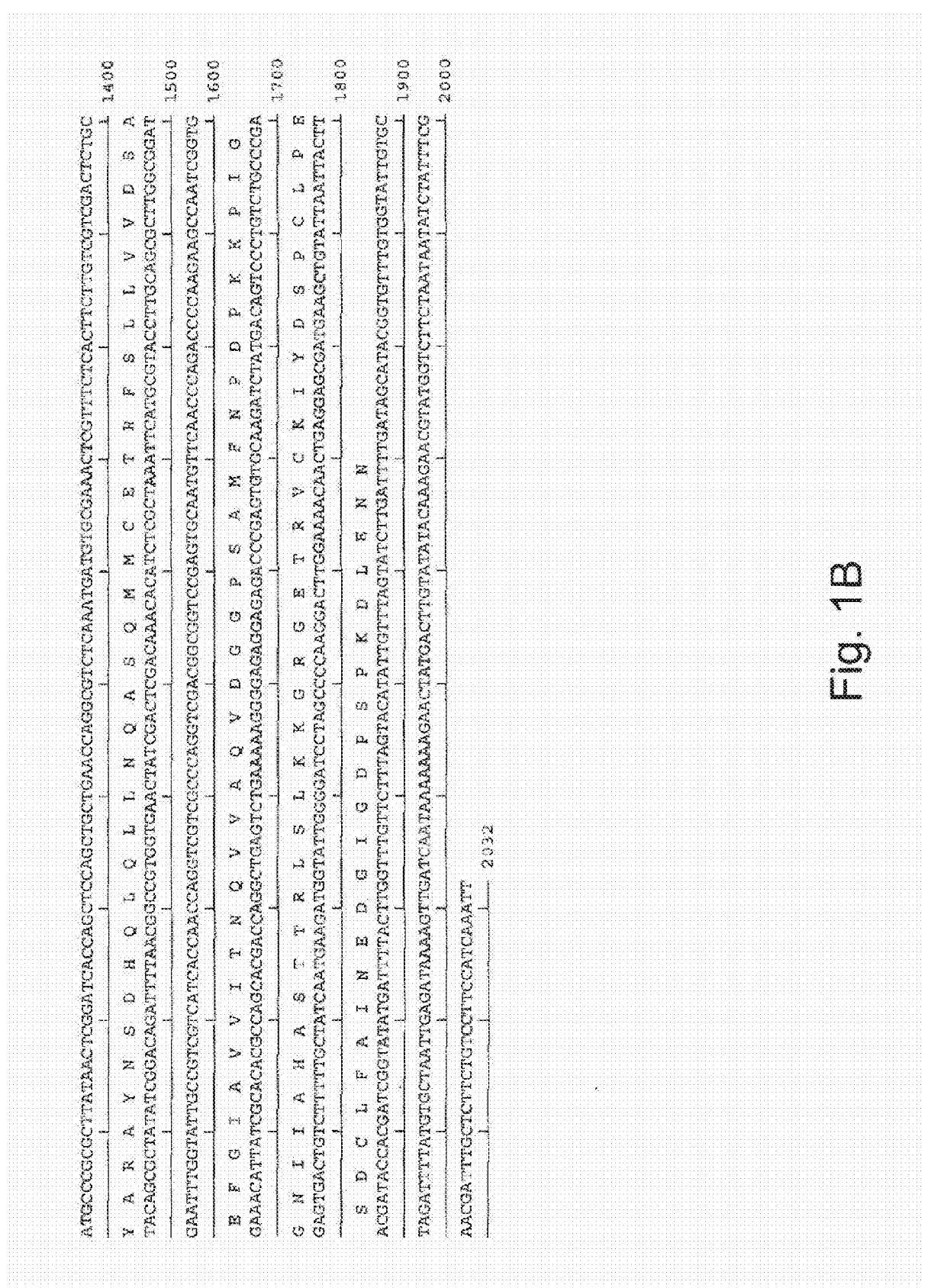

The 1.3 kb genomic region encompassing the coding sequence was sequenced to an average redundancy of 5.9. The nucleotide sequence and deduced amino acid sequence are shown in FIG. 1 (SEQ ID NOs: 1 and 2). Sequence analysis of the cloned insert revealed a coding sequence of 1307 bp (excluding the stop codon) encoding a protein of 348 amino acids. The coding sequence is punctuated by three introns of 97 bp, 98 bp, and 68 bp. The G+C content of the coding sequence is 55.3%. The predicted RDHA polypeptide has a molecular mass of 37.6 kdal and an isoelectric point of 5.24. Using the Signal P software program (Nielsen et al., 1997, *Protein Engineering* 10:1-6), no signal peptide was predicted (Y<0.027).

A comparative alignment of the *Aspergillus oryzae* RDHA protein sequence with other sequences using the Clustal W algorithm in the Megalign program of DNASTAR, showed that the deduced amino acid sequence of the *Aspergillus oryzae* RDHA protein shares 98% identity to the deduced amino acid sequence of the UVSC protein of *Emericella nidulans* (accession number CAB02454).

Clone 13 was deposited as *E. coli* pZL1rdhA13 (NRRL B-30503) on Jul. 27, 2001, with the Agricultural Research Service Patent Culture Collection, Northern Regional Research Center, 1815 University Street, Peoria, Ill.

Example 5

PCR Amplification of a Portion of the *Aspergillus oryzae* rdhb Gene

A portion of two *Aspergillus oryzae* genes homologous to the yeast rad52 gene were amplified by consensus/degenerate PCR (Rose et al., 1998, Nucleic Acids Res. 26: 1628-35). The amplification employed primers 980539 and 980540 shown below.

```
Primer 980539 (ANEVFGFNGW):
                                          (SEQ ID NO: 10)
5'-CGAACGAAGTCTTCGGTTTYAAYGGNTGG-3'

Primer 980540 (KKEGTTDGMK):
                                          (SEQ ID NO: 11)
5'-CTTCATGCCGTCGGTAGTNCCYTCYTTYTT-3'
```

The amplification reaction (30 µl) was prepared using *Aspergillus oryzae* HB425 genomic DNA as template with the following components: PCR buffer II (Perkin Elmer), 0.20 mM dNTPs, 0.4 µg of *Aspergillus oryzae* HowB425 genomic DNA, 5.0 µM primer 980539, 5.0 µM primer 980540, and 3.0 units of Taq DNA polymerase. Before amplification, the template DNA was denatured in a boiling water bath for 5 minutes and quick-cooled on ice. The reaction was initiated by adding Taq DNA polymerase to the other reaction components at 72° C. The reactions were incubated in a Stratagene Robocycler programmed for 35 cycles each for 30 seconds at 94° C., 60 seconds at 53° C., and 90 seconds at 72° C. (7 minutes final extension).

The amplification products were fractionated as described above for the rdhA gene, and bands at about 350 and 300 bp were excised and cloned using the TOPO TA cloning kit according to the manufacturer's instructions and the DNA sequence was determined using T7 promoter primer. DNA sequence analysis of the 350 and 300 bp gene segments showed that the amplified gene segments encoded a portion of two closely related *Aspergillus oryzae* genes, hereafter designated as rdhB (rad52 homolog B) and rdhC (rad52 homolog C), respectively.

Example 6

Isolation of a Full-Length *Aspergillus oryzae* rdhb Genomic Clone

Approximately 50 ng of the gel-purified ca. 300-bp product of the PCR amplification described in Example 3 was random-primer labeled using a Stratagene Prime-It II Kit according to the manufacturer's instructions and used to probe approximately 100,000 pfu of an *Aspergillus oryzae* genomic library constructed from *Aspergillus oryzae* strain HowB430 in the vector λZipLox using the same procedures described in Example 3.

Eleven hybridizing plaques were obtained, and four of these were purified, excised as pZL1 clones, and characterized as described in Example 3. The two unique clones obtained had insert sizes of approximately 3.9 kb and 6.3 kb. The larger clone was designated *E. coli* pZL1 clone #6 and submitted to sequence analysis (see Example 7).

Example 7

Characterization of the *Aspergillus oryzae* Genomic Clone Encoding RDHB

DNA sequencing of each clone was performed with an Applied Biosystems Prism 377 DNA Sequencer using the BigDye Terminator Cycle Sequencing Ready Reaction kit according to the manufacturer's instructions. Oligonucleotide sequencing primers were designed to complementary sequences in the pZL1 plasmid vector and were synthesized by Operon Technologies Inc., Alameda, Calif. Contig sequences were generated using a transposon insertion strategy (Primer Island Transposition Kit, Perkin-Elmer/Applied Biosystems, Inc., Foster City, Calif.).

Figure 2B:
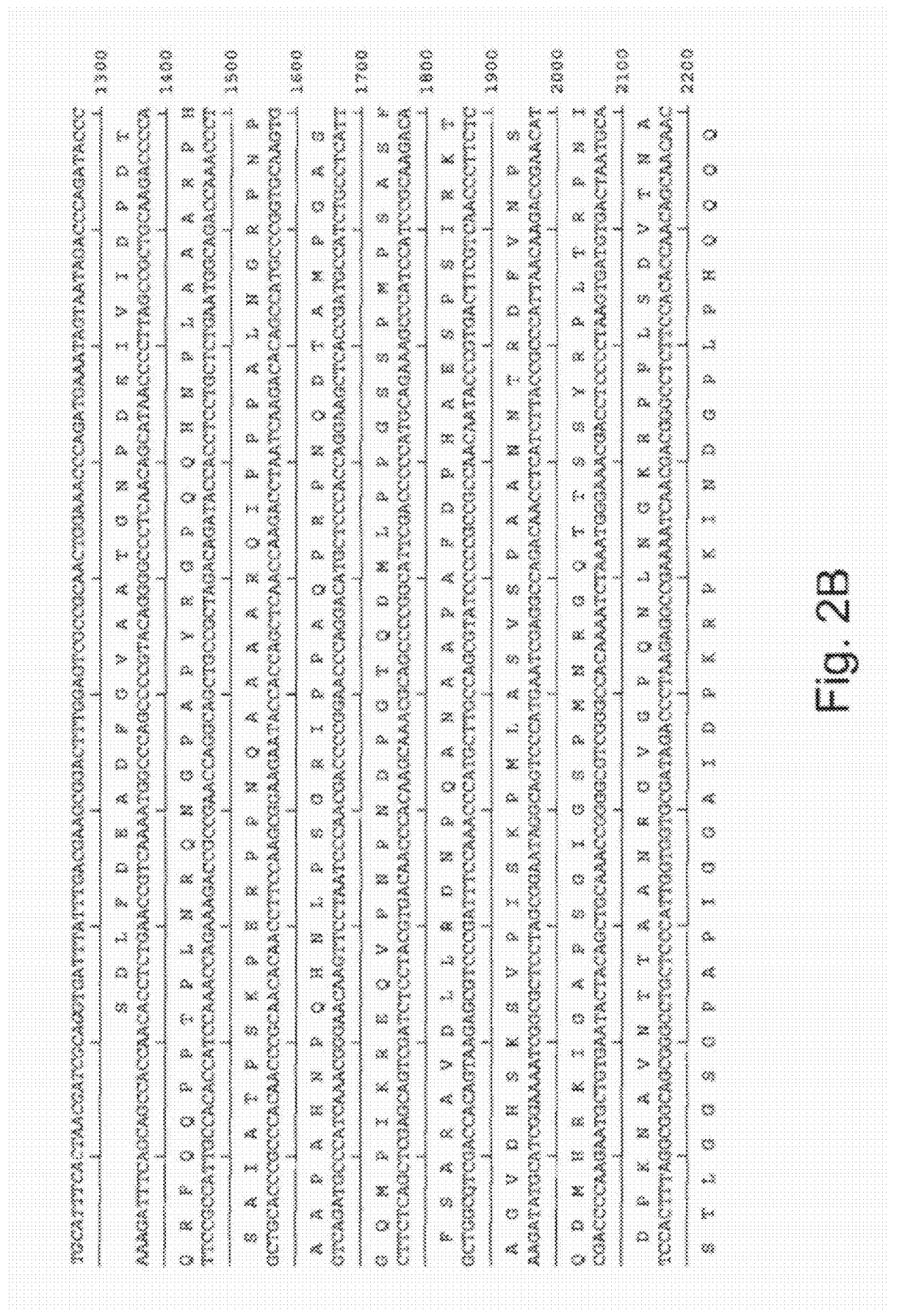
Figure 2C:
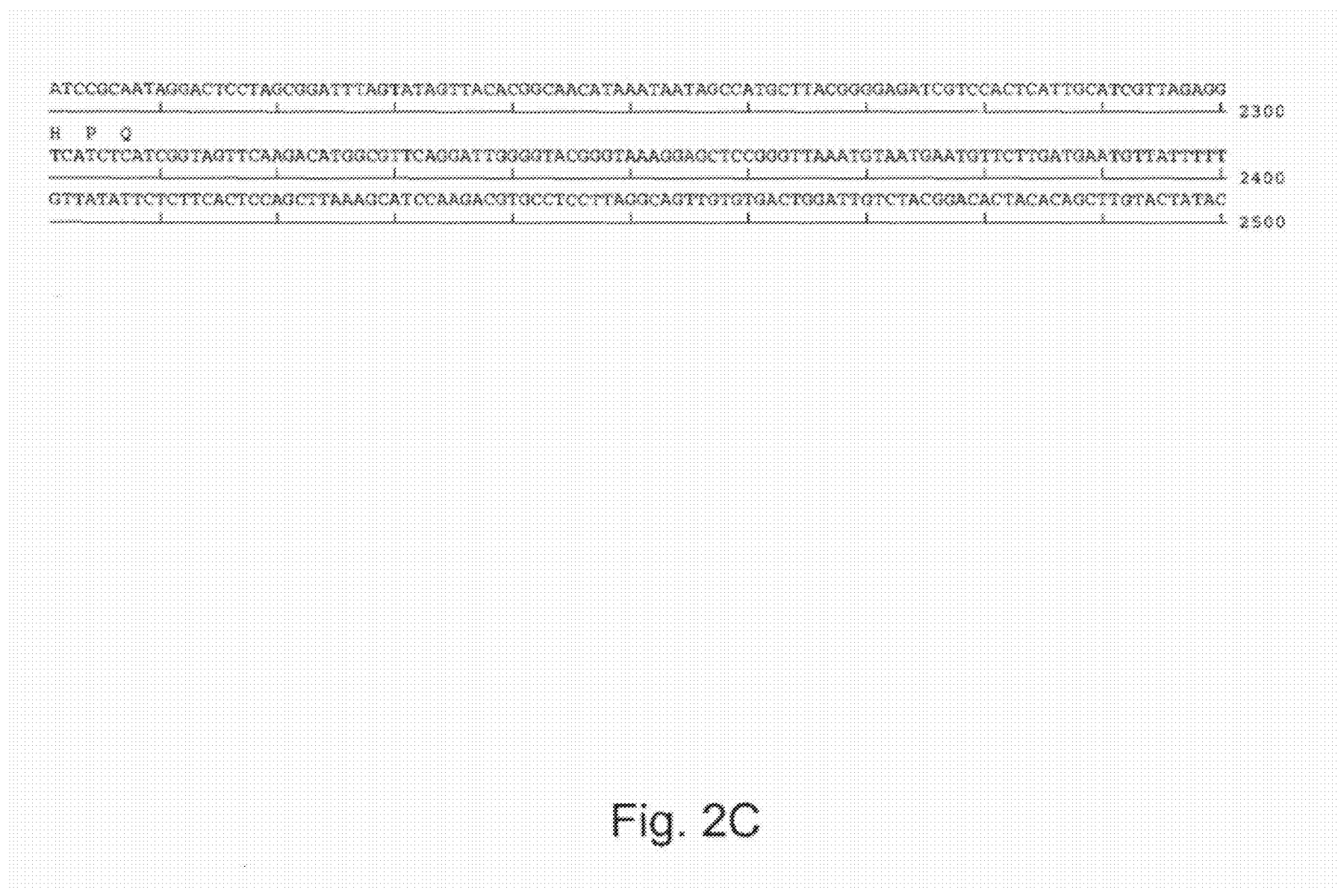

A 3257 bp genomic fragment was sequenced to an average redundancy of 4.7. The nucleotide sequence and deduced amino acid sequence are shown in FIG. 2 (SEQ ID NOs:3 and 4). Sequence analysis of the cloned insert revealed a coding sequence of 1946 bp (excluding the stop codon) encoding a protein of 565 amino acids. The coding sequence is punctuated by four introns of 78 bp, 65 bp, 56, and 52 bp. The G+C content of the coding sequence is 51.8%. The predicted RDHB polypeptide has a molecular mass of 60.7 kdal and an isoelectric point of 8.64. Using the SignalP software program (Nielsen et al., 1997, *Protein Engineering* 10:1-6), no signal peptide was predicted (Y<0.043).

A comparative alignment of the *Aspergillus oryzae* RDHB protein sequence with other sequences using the Clustal W algorithm in the Megalign program of DNASTAR, showed that the deduced amino acid sequence of the *Aspergillus oryzae* RDHB protein shares 33% identity to the deduced amino acid sequence of the RAD22 protein of *Schizosaccharomyces pombe* (accession number P36592) and 33% identity to the RAD52 protein of *Saccharomyces cerevisiae* (accession number P06778).

Clone #6 was deposited as *E. coli* pZL1rdhB6 (NRRL B-30504) on Jul. 27, 2001, with the Agricultural Research Service Patent Culture Collection, Northern Regional Research Center, 1815 University Street, Peoria, Ill.

Example 8

Construction of pRamB33

Intermediates pRaMB31 and pRaMB32 were constructed as follows: First, plasmid pUC19 was digested with NdeI plus PvuII and the 2241 bp vector fragment, purfied by agarose gel electrophoresis, was ligated with the following synthetic linker which contains restriction sites for MunI, PacI, BamHI, HindIII, PmeI, and MunI while inactivating the NdeI cloning site:

```
                                          (SEQ ID NO: 12)
5'-TATCAATTCTTAATTAAGGATCCAAGCTTGTTTAAACAATTC-3'

(SEQ ID NO: 13)
3'-AGTTAACAATTAATTCCTAGGTTCGAACAAATTTGTTAAC-5'-
```

The resulting pUC19-derivative was termed pRaMB31. Next, the *Aspergillus oryzae* pgk promoter and terminator regions (Genbank accession number D28484) as well as the bar gene from *Streptomyces hygroscopicus* (White et al. 1990, *Nucleic Acids Res.* 18: 1062) were amplified by PCR using the following primer pairs:

```
Aspergillus oryzae pgk promoter:
                                    (SEQ ID NO: 14)
5'-GATACATGTTATGGAGATGTTCTATCACACAAG-3'
(contains AflIII site)

(SEQ ID NO: 15)
5'-CAGGATCCTGCAGTATTGACTACTATGGT-3'
(contains BamHI site)

Aspergillus oryzae pgk terminator
                                    (SEQ ID NO: 16)
5'-CTGTTTAAACTGCAGGGAGGAACTGAAAAAGG-3'
(contains PmeI site)

(SEQ ID NO: 17)
5'-GTTAAGCTTGCGAAACGCAAATAATGTGTTG-3'
(contains HindIII site)

Streptomyces hygroscopicus bar gene
                                    (SEQ ID NO: 18)
5'-GTTACATGTCTCCAGAACGACGCCCGGCGGACATC-3'
(contains AflIII site)

(SEQ ID NO: 19)
5'-TGAAGCTTCAGATCTCGGTGACGGGCAG-3'
(contains HindIII site)
```

The amplification reactions (100 μl) was prepared using pMT1612 (which harbors the bar gene from *Streptomyces hygroscopicus*—EMBL accession number X05822) as template with the following components: 1× Pwo buffer (Roche Molecular Biochemicals, Indianapolis, Ind.), 0.25 mM dNTPs, 1.0 μM of each primer, and 5 units of Pwo DNA polymerase. The reactions were incubated in an Applied Biosystems thermocycler programmed for 1 cycle at 95° C. for 3 minutes, 45° C. for 2 minutes, and 67° C. for 5 minutes followed by 30 cycles each at 95° C. for 2 minutes; 45° C. for 2 minutes; and 67° C. for 2 minutes.

The PCR-amplified pgk terminator was digested with HindIII plus PmeI and the 635 bp product was purified by agarose gel electrophoresis, then ligated with pRaMB31 that had been cleaved with the same enzymes. The resulting intermediate plasmid was designated as pRaMB31.1. Next, the pgk promoter and bar gene segments were digested with BamHI plus AflIII and HindIII plus AflIII, respectively, and purified by electrophoresis. These two fragments were combined in a three-part ligation with the intermediate pRaMB31.1 that had been digested with BamHI plus HindIII. The product of this ligation, pRaMB32 contained the *Streptomyces hygroscopicus* bar gene under transcriptional control of the *Aspergillus oryzae* pgk promoter and terminator regions.

Next, the *Aspergillus oryzae* niaA promoter and alkaline protease (alp) terminator regions were amplified by PCR using high-fidelity Pwo polymerase (Boehringer-Mannheim, Indianapolis, Ind.) as above with the following primer pairs:

```
Aspergillus oryzae niaA promoter
                                    (SEQ ID NO: 20)
5'-GGTTAATTAACCGGCAGGGAAGGCCAATGAAAG-3'
(contains AflIII site)

(SEQ ID NO: 21)
5'-CCACGCGTATTTAAATGTCCGGGATGGATAGCACTGTGG-3'
(contains PacI site)

Aspergillus oryzae alp terminator
                                    (SEQ ID NO: 22)
5'-GGACGCGTGCGGCCGCGTACCAGGAGTACGTCGCAGG-3'
(contains MluI site)

(SEQ ID NO: 23)
5'-GGAGATCTGCAGCTGTGTACCAATAGAC-3'
(contains BglII site)
```

The amplified niaA promoter segment was cloned directly into pUC118 (Yanisch-Perron et al., 1985, *Gene* 33: 103-119), which had been digested with SmaI and dephosphorylated. Similarly, the alp terminator region was subcloned into pCR-blunt (Invitrogen, Carlsbad, Calif.). The nucleotide sequences of both products were determined to ensure accuracy. The niaA promoter fragment was isolated by gel electrophoresis following cleavage with PacI plus MluI, and the alp terminator segment was purified after digestion with MluI plus Bg/II. These purified fragments were mixed in a three-part ligation with pRaMB32 which had been previously cut with BamHI plus PacI. The resulting vector, designated as pRaMB33, contained (a) a selectable bar gene under the transcriptional control of the pgk promoter and terminator, and (b) unique NotI and SwaI restriction sites located between the niaA promoter and alp terminator for directional cloning of cDNA or other coding regions of interest.

Example 9

Construction of Expression Vector with niaA Promoter

Plasmid pRaMB33 was digested with XbaI and NruI to remove the Basta-resistance cassette. The remaining vector was isolated on a 0.8% agarose gel using TAE buffer where a 4.4 kb band was excised from the gel and purified using a QIAquick Gel Extraction Kit (QIAGEN, Chatsworth, Calif.) according to the manufacturer's instructions.

Figure 4:
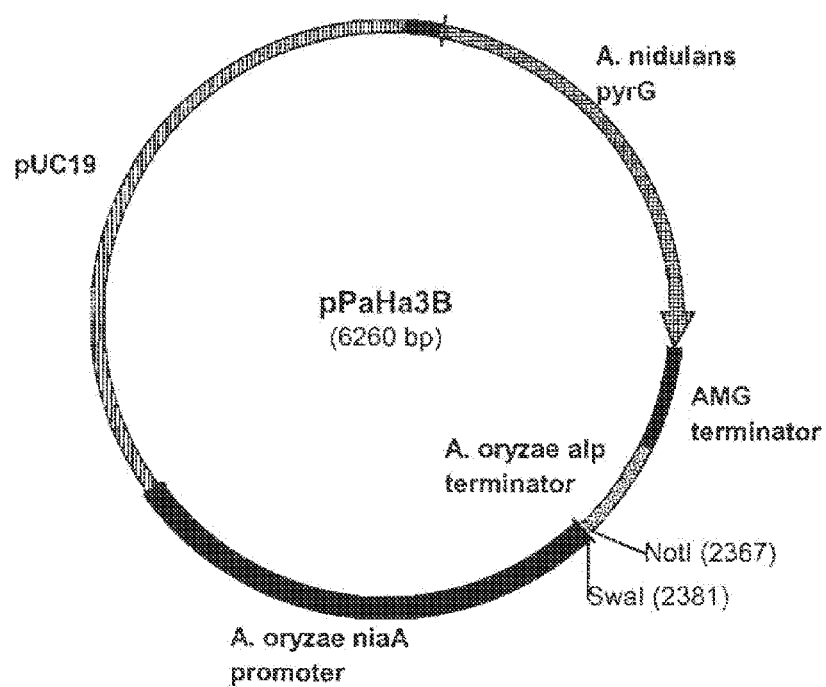
FIG. 4 shows a restriction map of pPaHa3B.

Plasmid pBANe13 (WO 97/47746) was digested with PmeI and NheI, and the fragment containing the pyrG gene and AMG terminator was similarly gel isolated and purified. The fragments were mixed together, blunt-ended using Klenow polymerase, ligated, and transformed into *E. coli* DH5α. Plasmid DNA was prepared from ten of the resulting transformants, and one displaying the correct restriction digest pattern was designated pPaHa3B (FIG. 4). The niaA promoter is induced by nitrate.

Example 10

Plasmids for Inter-Plasmid Recombination Assay

Plasmid pSMO122 (U.S. Pat. No. 5,958,727) was digested with HindIII and treated with bacterial alkaline phosphatase. Plasmid Arp1 (Gems et al., 1991, *Gene* 98: 61-67) was digested with HindIII and the digest fractionated on a 1.0% agarose gel in TAE buffer. A 5.8 kb fragment was excised from the gel and purified using a QIAquick Gel Extraction Kit (QIAGEN, Chatsworth, Calif.) according to the manufacturer's instructions. This fragment was ligated to the linearized pSMO122 plasmid and transformed into *Escherichia coli* DH5α. Plasmid DNA was prepared from transformants, and one, showing the correct fragment sizes after digestion with HindIII, was designated pHB217. The fragment contains the AMA1 replication region from *Emericella nidulans* and the pyrG gene from *Aspergillus oryzae*.

Figure 5:
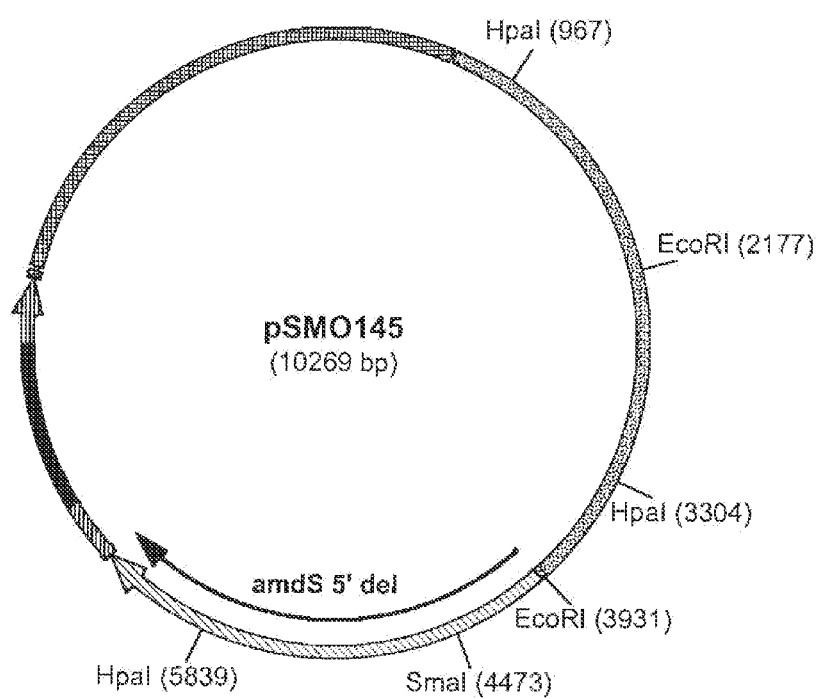
FIG. 5 shows a restriction map of pSMO145.

Plasmid pPaHa1-1 was digested NsiI and the ends were made blunt using T4 DNA polymerase. The products were fractionated on a 0.8% agarose gel using TAE buffer and a 2 kb band was excised from the gel and purified using a QIAEX Gel Extraction Kit (QIAGEN, Chatsworth, Calif.) according to the manufacturer's instructions. The fragment was then inserted into the SmaI site of pHB217. The plasmid was designated pSMO145 (FIG. 5). The plasmid carries a 220 bp deletion of the *Emericella nidulans* amdS gene encompassing a portion of that gene's promoter, all of the 5'-untranslated region, and 132 bp of the coding region.

Plasmid pToC202 (FIG. 6) was constructed to contain three up promoter mutations have identified within the *Aspergillus nidulans* amdS gene: The I666 and I66 up mutations have been described by Katz et al., 1990, *Mol. Gen. Genet.* 220: 373-376. The I9 mutation has been described by Davis and Hynes, 1989, *TIG* 5: 14-19 and by Todd, 1998, *EMBO* 17: 2042-2054. Plasmid pI66PI9 contains the *Aspergillus nidulans* amdS with the two up promoter mutations I66 and I9. The amdS allele of this plasmid was subcloned into pUC19 as a 2.7 kb XbaI fragment to form the plasmid pToC186C. (Yanisch-Perron et al., 1985, *Gene* 33 103-119).

Figure 6:
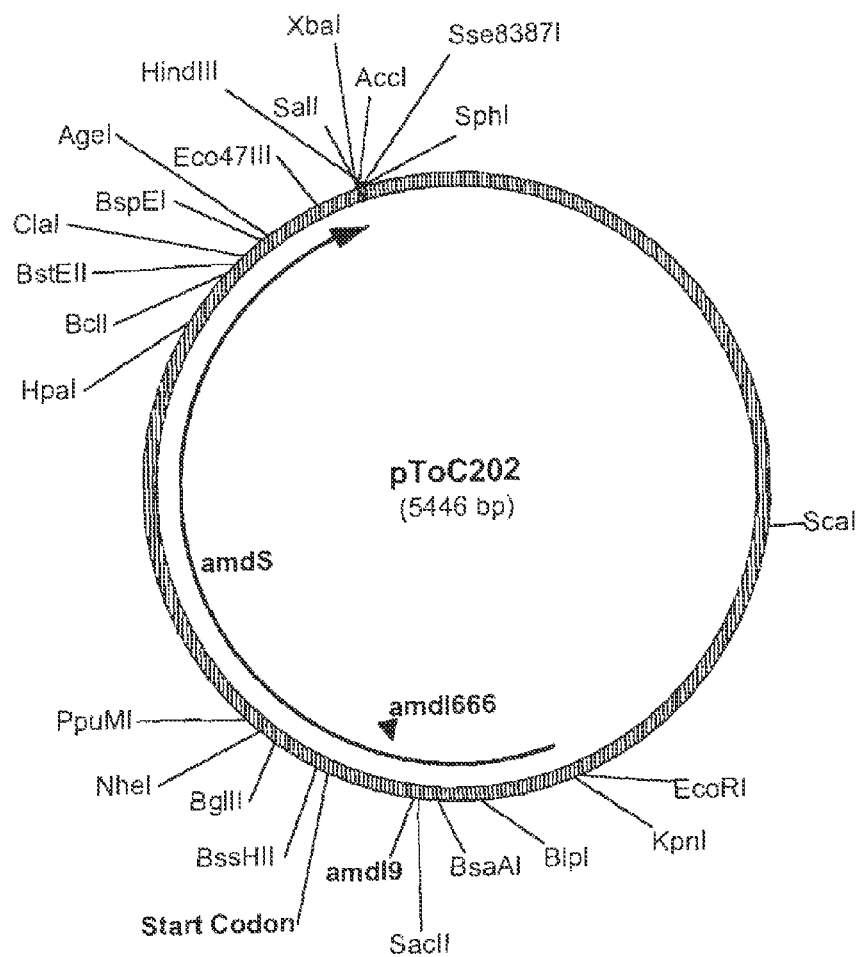
FIG. 6 shows a restriction map of pToC202.

Plasmid pMSX-6B1 contains the *Aspergillus nidulans* amdS gene with the up promoter mutation I666. The amdS allele of this plasmid was subcloned into pUC19 as a 2.7 kb XbaI fragment to form the plasmid pToC196. The I9 and I666 mutations were combined by inserting a 544 bp XmaI fragment from pToC186 harboring the I9 mutation into the 4903 bp XmaI fragment of pToC196 to form the plasmid pToC202 (FIG. 6).

Figure 7:
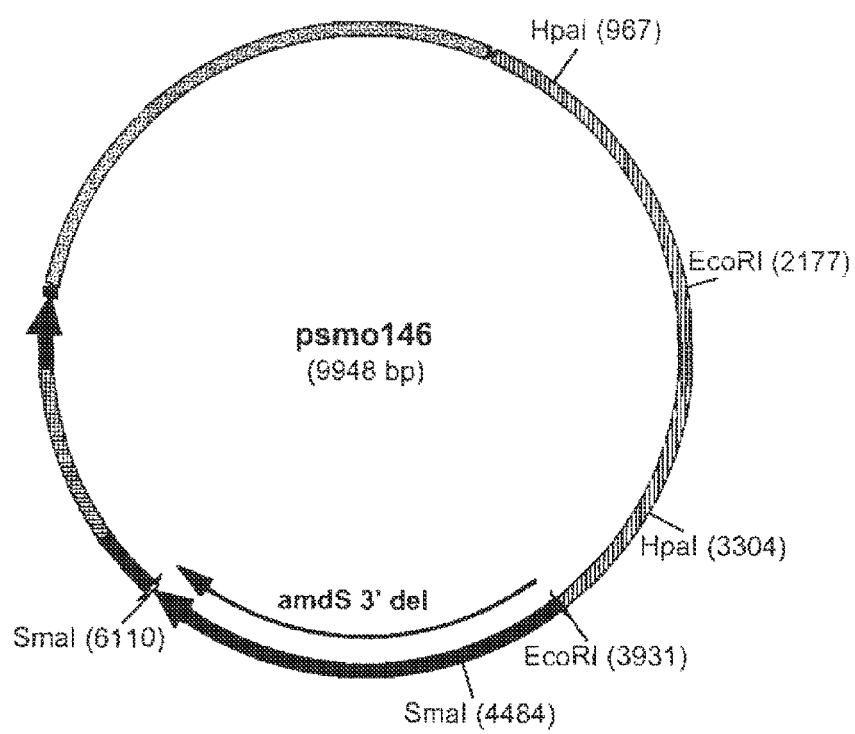
FIG. 7 shows a restriction map of pSMO146.

A 3' truncation of the *Emericella nidulans* amdS gene was produced by digesting plasmid pToC202 with EcoRI and HpaI, blunting with Klenow fragment, gel and purified using a QIAEX Gel Extraction Kit according to the manufacturer's instructions. The fragment was then inserted into the SmaI site of pHB217. The resulting plasmid was designated pSMO146 (FIG. 7). The promoter region of amdS in this construct contained mutations that enhance promoter strength, allowing good growth on acetamide as the sole nitrogen source with a single copy of the gene.

Example 11

Construction of *Aspergillus oryzae* rdhA and rdhB Overexpression Vectors

Plasmid pRaMB32 (described in Example 8) was digested with PstI and ScaI and fractionated on a 1% agarose gel. The 2.8 kb band containing the pgk promoter, bar gene, and pgk terminator was excised and purifed with the Qiagen QIAEX II kit (QIAGEN, Chatsworth, Calif.) according to the manufacturer's instructions. Plasmid pBANe8 (U.S. Pat. No. 5,958,727) was digested with NsiI and dephosphorylated using 150 units of bacterial alkaline phosphatase followed by heat inactivation at 65° C. for 1 hour. The digest was fractionated on a 1% agarose gel and the 5.0 kb band was excised and purified as above. The two fragments were ligated together and transformed into *E. coli* XL10 Gold cells (Stratagene, La Jolla, Calif.) according to the manufacturer's instructions. Plasmid DNA was prepared from transformants and screened for correctness by digesting with StuI. One plasmid showing the correct digestion pattern was named pBANe44.

The 1.3 kb coding region of the *Aspergillus oryzae* rdhA gene was amplified by PCR from *E. coli* pZL1 clone #13. Primers incorporated SwaI, PacI, or NotI sites for subsequent cloning and had the following sequence:

```
Sense Swa primer (980442):
                                      (SEQ ID NO: 24)
5'-CATTTAAATGATGACGGCGGATATG-3'

Antisense Pac primer (980359):
                                      (SEQ ID NO: 25)
5'-GTTAATTAATCAGTTGTTTTCCAAGTC-3'

Antisense Not primer (980451):
                                      (SEQ ID NO: 26)
5'-AGCGGCCGCTCAGTTGTTTTCCAAGTC-3'
```

The amplification reaction (50 µl) was composed of the following components: 1× Pwo buffer (Roche Molecular Biochemicals, Indianapolis, Ind.), 0.2 mM dNTPs, 1.0 µM of each primer, 5 units of Pwo DNA polymerase, and approximately 60 ng of heat-denatured clone #13. The reactions were incubated in a Perkin-Elmer Model 480 Thermal Cycler programmed as follows: 22 cycles each at 94° C. for 45 seconds; 55° C. (52° C. for first two cycles) for 45 seconds; 72° C. for 90 seconds, and a final extension at 72° C. for 7 minutes.

The products were fractionated on a 0.8% agarose gel using TAE buffer, and the predominant band at 1.3 kb was excised and purified using the QIAquick Gel Extraction Kit. The products were cloned into pCR®2.1-TOPO (Invitrogen, Carlsbad, Calif.) after addition of 3' A-overhangs according to the manufacturer's suggested protocol.

The 1.3 kb insert from one randomly selected clone was removed by sequential digestion with SwaI and PacI (TAKA promoter construct) or NotI (niaA promoter construct), gel purified, and ligated into similarly digested pBANe13, pBANe44, or pPaHa3B. The ligation mixtures were transformed into *E. coli* DH5α, and clones were screened for the correct inserts by digestion with SwaI and PacI or SwaI and NotI. Miniprep DNA was sequenced from the ends of both inserts and shown to contain the full rdhA coding sequence. The constructs were designated pBANe13rad51, pSMO143, and pPaHa3Brad51.

The 1.96 kb coding region of rdhB was amplified essentially as described above using pZL1 clone #6 and the following primers:

```
Sense SwaI primer (980924):
                                      (SEQ ID NO: 27)
5'-ATTTAAATGATGCCCAACACGACAGACA-3'

Antisense PacI primer (980925):
                                      (SEQ ID NO: 28)
5'-TTAATTAACTATTGCGGATGTTGTTGCT-3'

Antisense NotI primer (980826):
                                      (SEQ ID NO: 29)
5'-GCGGCCGCCTATTGCGGATGTTGTTGC-3'
```

The annealing temperature for the PCR was 60° C. (58° C. for first two cycles). The DNA was subcloned into pCR-Blunt (Invitrogen, Carlsbad, Calif.), and miniprep DNA from clones containing the correct inserts was cloned into pBANe13, pBANe44, pRaMB33, or pPaHa3B as described above. The resulting constructs were named pBANe13rad52, pSMO145, pSMO155 and pPaHa3Brad52, respectively.

Example 12

Construction of *Aspergillus oryzae* PaHa29

*Aspergillus oryzae* hemA 5'-deletion strain SE29-70 (Elrod et al., 2000, *Current Genetics* 38:291-298) was cultured on PDA plates containing 5-aminolevulinic acid and uridine to allow for loss of the pyrG gene. Spores from this plate were then plated on minimal plates containing fluoroorotic acid (FOA), uridine, and 5-aminolevulinic acid. Eight FOA-resistant colonies were spore purified on minimal plates containing 5-aminolevulinic acid and uridine. One of the FOA-resistant colonies was verified as having a pyrG deletion phenotype by lack of growth on minimal medium containing 5-aminolevulinic acid and by recovery of prototrophy after transformation of protoplasts (prepared as in Example 13)

with an autonomously-replicating plasmid carrying the pyrG gene (pHB217). This strain was designated *Aspergillus oryzae* PaHa29.

Example 13

Construction of *Aspergillus oryzae* HowB423 and HowB425

Protoplasts of *Aspergillus oryzae* HowB101 were transformed with pSMO143 or pSMO145 and plated on Basta transformation plates.

Protoplasts of *Aspergillus oryzae* strain HowB101 were prepared according to the method of Christensen et al., 1988, *Bio/Technology* 6: 1419-1422. The transformation was conducted with protoplasts at a concentration of ca. $2 \times 10^7$ protoplasts per ml. One hundred µl of protoplasts were placed on ice for 5 minutes with ca. 2 µg of the pSMO143 or pSMO145; 250 µl of 60% polyethylene glycol 4000, 10 mM Tris-HCl, pH 7.5, 10 mM $CaCl_2$ was added, and the protoplasts were incubated at 37° C. for 30 minutes. Three mls of STC (1.2 M sorbitol, 10 mM Tris-HCl, pH 7.5, and 10 mM $CaCl_2$) was added. The solution was mixed gently and poured onto 150 mm Basta transformation plates (per liter: 0.52 g of KCl, 0.52 g of $MgSO_4.7H_2O$, 1.52 g of $KH_2PO_4$, 1 ml of trace metals described below, 342.3 g of sucrose, 25 g of Noble agar, 10 ml of 1 M urea, 10 ml of 5 mg/ml Basta). The trace metals solution (1000×) was comprised of 22 g of $ZnSO_4.7H_2O$, 11 g of $H_3BO_3$, 5 g of $MnCl_2.4H_2O$, 5 g of $FeSO_4.7H_2O$, 1.6 g of $CoCl_2.5H_2O$, 1.6 g of $(NH_4)_6Mo_7O_{24}$, and 50 g of $Na_4EDTA$ per liter. Plates were incubated 5-7 days at 34° C. until colonies appeared. Putative transformants were spore purified twice on the same medium.

Example 14

Construction of hemA 3'-Deletion

Figure 8:
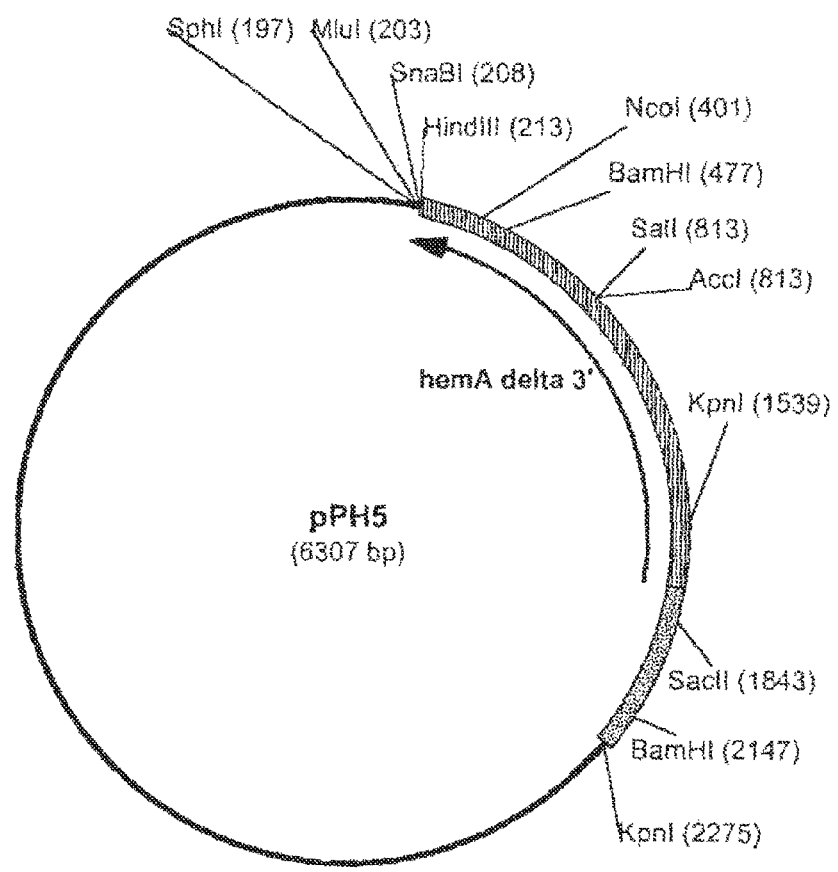
FIG. 8 shows a restriction map of pPH5.

Plasmid pSE17 (WO 97/47746) was digested with HindIII to remove a portion of the hemA coding sequence and all of the 3' flanking sequence to produce a 6.3 kb fragment. The 6.3 kb fragment was run on a 0.8% agarose gel in TAE buffer, excised, and purifed using a QIAEX II Gel Extraction Kit (QIAGEN, Chatsworth, Calif.) according to the manufacturer's instructions. The fragment was recircularized by ligation and transformed into *E. coli* XL1-Blue cells to yield plasmid pPH5 (FIG. 8).

Figure 9:
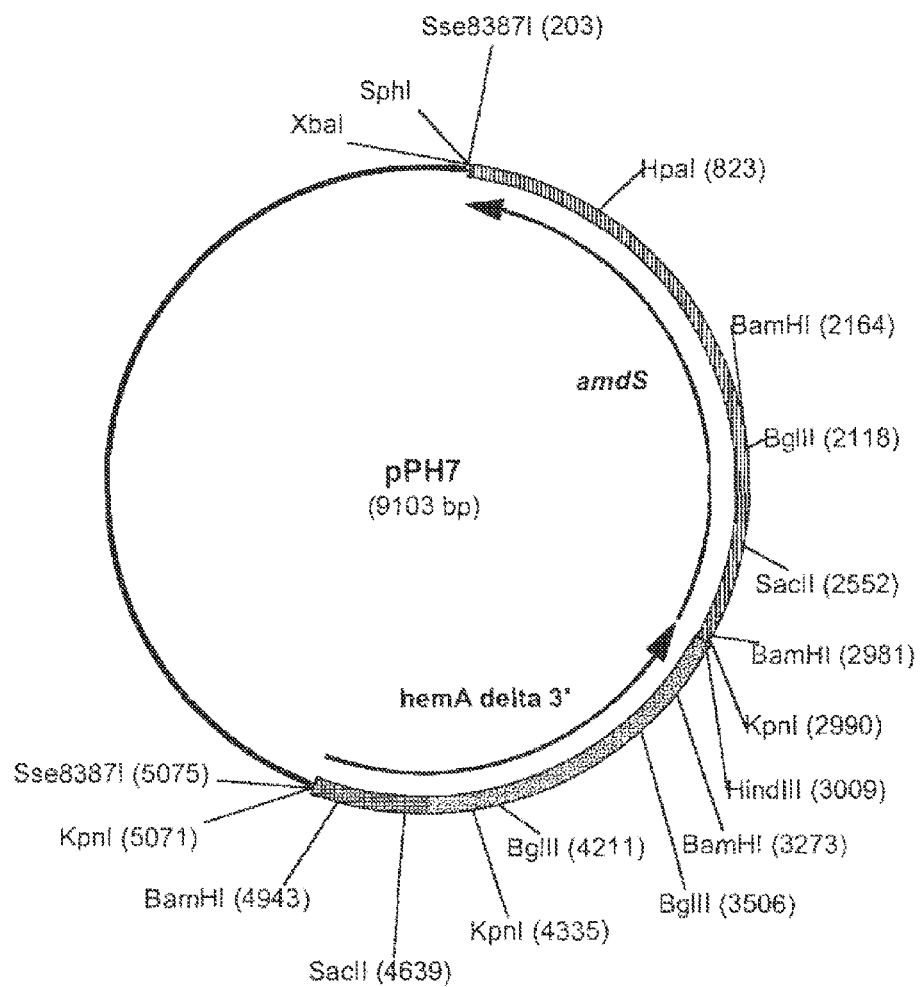
FIG. 9 shows a restriction map of pPH7.

The amdS gene from *Emericella nidulans* was isolated from pToC202 bp digestion with EcoRI, Klenow fill-in, digestion with SphI, and gel purification as above. The amdS gene fragment was ligated into pPH5 digested with SphI and SnaBI and similarly gel purified. The ligation mixture was transformed into *E. coli* XL1-Blue cells and plasmid DNA was prepared from twenty-four transformants. One plasmid DNA preparation showing the correct size fragments upon digestion with SacI, KpnI, or BamHI was designated pPH7 (FIG. 9).

Example 15

Construction of hemAA Strains Overexpressing rdhA or rdhB

Protoplasts of *Aspergillus oryzae* PaHa29 were prepared as described in Example 13 and transformed with several µg of supercoiled pBANe13rad51, pBANe13rad52, pPaHa3Brad51, or pPaHa3Brad52, and plated on minimal medium containing 30 µg/ml 5-aminolevulinic acid. Individual transformants were spore purified on MMGAS (per liter: 0.5 g of NaCl, 0.5 g of $MgSO_4.7H_2O$, 2.0 g of $KH_2PO_4$, 1.2 g of $K_2HPO_4$, 1 ml of trace metals described below, 218 g of sorbitol, 20 g of Noble agar, 3.7 g of $NH_4Cl$, 0.1 ml of 1.0 M $CaCl_2$, and 10 ml of glycerol) plus 5-aminolevulinic acid (pBANe13 transformants) or MMASM (per liter: 0.5 g of NaCl, 0.5 g of $MgSO_4.7H_2O$, 2.0 g of $KH_2PO_4$, 1.2 g of $K_2HPO_4$, 1 ml of trace metals described below, 20 g of sucrose, 20 g of Noble agar, 3.7 g of $NH_4Cl$, and 0.1 ml of 1.0 M $CaCl_2$) plus 5-aminolevulinic acid (pPaHa3B transformants). The trace metals solution (1000×) was comprised of 10 g of $ZnSO_4.7H_2O$, 0.4 g of $CuSO_4.5H_2O$, 0.04 g of $Na_2B_4O_7.10H_2O$, 0.7 g of $MnSO_4.H_2O$, 1.2 g of $FeSO_4.7H_2O$, 1.6 g of $CoCl_2.5H_2O$, and 0.8 g of $Na_2MoO_2.2H_2O$ per liter. Respective transformants from the indicated plasmids were designated PaHa30, PaHa31, PaHa32, and PaHa33. Multiple transformants of each were generated and are designated by appending a number, e.g., PaHa31-2.

Example 16

Effect of rdhA or rdhB Overexpression on Interplasmid Recombination

*Aspergillus oryzae* grows very poorly using acetamide as the sole nitrogen source. Growth can be greatly enhanced by introduction of one or more copies of the amdS gene from *Emericella nidulans*. This characteristic was used to monitor inter-plasmid recombination by co-transforming *Aspergillus oryzae* protoplasts with two autonomously-replicating plasmids, one carrying a deletion in the 5' region of amdS (pSMO145), and the other carrying a deletion in the 3' region (pSMO146). Vigorous growth of transformants on acetamide can only be achieved following homologous recombination between the different plasmids to reconstitute at least one complete amdS gene. Both plasmids also carry the pyrG gene in order to assess relative transformation efficiency.

The frequency of recombination in parental (*Aspergillus oryzae* HowB101) and rdhA (*Aspergillus oryzae* HowB443) or rdhB (*Aspergillus oryzae* HowB445) over-expression strains was assessed by co-transforming with both plasmids and plating on minimal medium with either nitrate or acetamide as the sole nitrogen sources (Table 1). The sucrose in these plates partially induces the TAKA promoter. Protoplasts of the indicated strains were prepared as described in Example 13 and co-transformed with 1.5 µg each of pSMO145 and pSMO146. A portion of the protoplasts was plated on minimal medium with either nitrate or acetamide as the sole nitrogen source, and the number of colonies was counted after six days of incubation at 37° C. Minimal nitrate plates were composed per liter of 6 g of $NaNO_3$, 0.52 g of KCl, 6.08 g of $KH_2PO_4$, 0.5 g of $MgSO_4.7H_2O$, 342.3 g of sucrose, 10 g of glucose, 0.004 g of biotin, 20 g of noble agar, and 1 ml of the trace metals described in Example 15. The medium was adjusted to pH 6.5 with NaOH. Minimal acetamide plates (COVE) were composed per liter of 10 mM acetamide, 15 mM CsCl, 0.52 g of KCl, 1.52 g of $KH_2PO_4$, 0.52 g of $MgSO_4.7H_2O$, 342.3 g of sucrose, 25 g of noble agar, and 1 ml of trace metals. Transformation with either plasmid alone yielded no transformants on acetamide. Overall transformation efficiency of the over-expressing strains was somewhat reduced compared to the parental strain, however, inter-plasmid recombination frequencies were elevated by 14 and 26-fold in the rdhA and rdhB over-expression strains, respectively. In *Aspergillus oryzae* HowB445, plasmids in almost half of the total transformants presumably underwent at least one homologous recombination event that reconstituted a functional amdS gene.

TABLE 1

Stimulation of interplasmid recombination in rdhA or rdhB overexpressing strains.

|  | HowB101 | HowB443 | HowB445 |
|---|---|---|---|
| Transformants per ng, nitrate (pyrG selection) | 3.43 | 1.83 | 1.33 |
| Transformats per ng, acetamide (amdS and pyrG selection) | 0.06 | 0.46 | 0.61 |
| Recombination frequency | 0.018 | 0.251 | 0.456 |
| Fold stimulation | 1.0 | 14.4 | 26.1 |

Example 17

Effect of rdhA or rdhB Overexpression on Interchromosomal Recombination

The hemA gene of *Aspergillus oryzae* codes for 5-aminolevulinate synthase, the first enzyme in heme biosynthesis. Mutants lacking this enzyme are unable to grow unless the medium is supplemented with 5-aminolevulinic acid. The native hemA gene in the rdhB overexpressing *Aspergillus oryzae* strain PaHa31-2 has been replaced by hemA carrying a 445-bp deletion in the 5' region of the coding sequence according to the procedure described in U.S. Pat. No. 6,100, 057, and thus this strain will not grow on minimal medium. Protoplasts of *Aspergillus oryzae* PaHa31-2 were transformed with 5 µg of plasmid pPH7 (Example 14) using the protocol described in Example 13. This plasmid carries the hemA gene with a deletion of all of the 3'-untranslated region and the last 382 bp of the coding region. The plasmid also contains the *E. nidulans* amdS gene, and transformants were therefore initially selected on COVE plates (Example 16) containing 20 µg/ml of 5-aminolevulinic acid. One specific transformant that grew on COVE, but still required 5-aminolevulinic acid for growth, was spore purified twice and designated *Aspergillus oryzae* PaHa31-2.2.

Spores from transformant *Aspergillus oryzae* PaHa31-2.2 were plated on MMGU medium (MMGAS (Example 15) without sorbitol and with 10 mM urea in place of $NH_4Cl$) containing increasing concentrations of maltose in order to induce expression of rdhB in a controlled fashion. Growth on this medium can only occur if homologous recombination occurs between the single-copy chromosomal hemA∆5'-gene and the chromosomally-integrated plasmid carrying the hemA∆3' gene.

The results demonstrated that induction of rdhB expression greatly increased the frequency of homologous recombination. Concentrations of maltose as low as 0.02% had an obvious stimulatory effect. Most of the colonies were very slow to first appear and also grew very slowly, even when transferred to new plates not containing maltose. However, these colonies grew fairly normally when the medium was supplemented with 5-aminolevulinic acid, indicating that the complementation for hemA deficiency was only partial. Most likely this resulted from a gene conversion event that restored the coding region of hemA in one of the hemA3' gene copies, but failed to restore the 3'-untranslated region. This could result in relatively low-level expression and incomplete complementation.

The low concentrations of maltose required to achieve marked stimulation of hemA+ colony formation suggested that relatively mild induction of rdhB transcription was sufficient to maximally promote homologous recombination. Also, transcription from the TAKA promoter was not completely suppressed in glycerol, and thus the background levels of recombination seen on glycerol may at least partially reflect this lack of complete suppression. To overcome this, strains were created wherein rdhA (PaHa32) or rdhB (PaHa33) was expressed under control of the weaker niaA promoter. The 3'-deleted copy of hemA carried on plasmid pPH7 was introduced into these strains in a manner identical to that described above for creation of PaHa31-2.2. The specific transformants selected for testing were designated *Aspergillus oryzae* PaHa32-4.6 and PaHa33-5.1.

Approximately $2 \times 10^7$ spores of PaHa32-4.6 or PaHa33-5.1 were plated on either MMASM (Example 15) or MMNSM (MMASM with 10 mM $NaNO_3$ in place of $NH_4Cl$). The former medium keeps the niaA promoter turned off and the latter medium induces the niaA promoter and hence stimulates transcription of the rdhA or rdhB gene. The appearance of colonies was monitored for 7 days. The results demonstrated that interchromosomal recombination is stimulated by an elevation in transcription of either rdhA or rdhB.

Example 18

PCR Amplification of a Portion of the *Aspergillus oryzae* rdhd Gene

A portion of the *Aspergillus oryzae* rdhD (rad54 homolog D) gene was amplified by nested degenerate PCR. The amplification employed primers 980057, 980058, 980059 and 980060 shown below.

```
Primer 980057:
5'- GAYCCIGAYTGGAAYCCNG -3'          (SEQ ID NO: 30)

Primer 980058:
5'- TTYTTYTGICCRTCNCKCCA -3'         (SEQ ID NO: 31)

Primer 980059:
5'- AAYTAYACICARACNYTNGA -3'         (SEQ ID NO: 32)

Primer 980060:
5'- ATITTYTCYTCDATNGTNC -3'          (SEQ ID NO: 33)
```

The first amplification reaction (30 µl) was prepared using *Aspergillus oryzae* HB101 genomic DNA as template with the following components: PCR buffer II (Perkin Elmer), 0.20 mM dNTPs, 0.4 µg of *Aspergillus oryzae* HowB101 genomic DNA, 5.0 µM primer 980059, 5.0 µM primer 980060, and 3.0 units of Taq DNA polymerase. Before amplification, the template DNA was denatured in a boiling water bath for 5 minutes and quick-cooled on ice. The reaction was initiated by adding Taq DNA polymerase to the other reaction components at 72° C. The reactions were incubated in a Stratagene Robocycler programmed as follows: 35 cycles each for 45 seconds at 94° C., 45 seconds at 39, 41, or 43° C., and 60 seconds at 72° C. (7 minutes final extension). Reaction products were pooled, precipitated with 2 volumes of ethanol, dried, and dissolved in 10 µl of TE. The second amplification reaction (30 µl) was prepared using the product of the first amplification as template with the following components: PCR buffer II (Perkin Elmer), 0.20 mM dNTPs, 0.2 µl of template DNA, 5.0 µM primer 980057, 5.0 µM primer 980058, and 3.0 units of Taq DNA polymerase. Before amplification, the template DNA was denatured in a boiling water bath for 5 minutes and quick-cooled on ice. The reaction was initiated by adding Taq DNA polymerase to the other reaction components at 72° C. The reactions were incubated in a Stratagene Robocycler programmed as follows: 35 cycles each for 45 seconds at 94° C., 45 seconds at 46, 48, 50, or 52° C., and 60 seconds at 72° C. (7 minutes final extension).

A portion of the reaction products was fractionated on a 3% agarose gel, and bands at about 70 bp were excised and purified using QIAquick with a final elution volume of 30 µl. Approximately 2 µl of this product was reamplified under the same PCR conditions and fractionated and purified in the same manner. The ca. 70 bp fragment was cloned using the TOPO TA cloning kit according to the manufacturer's instructions and the DNA sequence was determined using T7 promoter primer. DNA sequence analysis of the 68 bp gene segment showed that the amplified gene encoded a portion of the *Aspergillus oryzae* rdhD gene. The sequence from this clone was used to design a non-degenerate primer to be used for amplification of a larger region of the rdhD gene. The employed primer is shown below.

```
Primer 980866:
5'- AATGCTTGTTGATCAGCAG -3'    (SEQ ID NO: 34)
```

The amplification reaction (120 µl) was prepared using *Aspergillus oryzae* HB425 genomic DNA as template with the following components: PCR buffer II (Perkin Elmer), 0.25 mM dNTPs, 2.0 µg template DNA, 4.2 µM primer 980059, 0.4 µM primer 980866, and 5.0 units of Taq DNA polymerase. Before amplification, the template DNA was denatured in a boiling water bath for 5 minutes and quick-cooled on ice. The reaction was initiated by adding Taq DNA polymerase to the other reaction components at 72° C. The reactions were incubated in a Stratagene Robocycler programmed as follows: 30 cycles each for 45 seconds at 94° C., 45 seconds at 39, 41, 43, or 45° C., and 60 seconds at 72° C. (7 minutes final extension). The ca. 250 bp product was fractionated on an agarose gel, excised, and purified using the QIAquick system. Three µl of the purified fragment was reamplified under the same PCR conditions for 25 cycles at an annealing temperature of 40° C., and the product was gel purified in the same manner. Direct sequencing of the PCR product using primer 980866 demonstrated that the gene fragment encoded a portion of the rdhD gene.

Example 19

Isolation of Partial-Length *Aspergillus oryzae* rdhD Genomic Clones

Genomic libraries were prepared and plated as in Example 3. The PCR product of 232 bp described in Example 18 was radioactively labeled using the Strategene Prime-It II kit according to the manufacturer's protocol with the exception that the random primers were replaced by 0.6 µM of primer 866. The labeled product was used to probe approximately 100,000 pfu of an *Aspergillus oryzae* genomic library constructed from *Aspergillus oryzae* strain HowB430 in the vector λZipLox using the same procedures described in Example 3.

Eleven hybridizing plaques were obtained, and four of these were purified, excised as pZL1 clones, and characterized as described in Example 3.

Example 20

Characterization of the *Aspergillus oryzae* Genomic Clone Encoding RDHD

DNA sequencing of each clone was performed with an Applied Biosystems Prism 377 DNA Sequencer using the BigDye Terminator Cycle Sequencing Ready Reaction kit according to the manufacturer's instructions. Oligonucleotide sequencing primers were designed to complementary sequences in the pZL1 plasmid vector and were synthesized by Operon Technologies Inc., Alameda, Calif. Contig sequences were generated using a transposon insertion strategy (Primer Island Transposition Kit, Perkin-Elmer/Applied Biosystems, Inc., Foster City, Calif.).

A 5514 bp genomic fragment was sequenced to an average redundancy of 6.0, and includes sequences from all of the genomic clones. No single clone contained the entire gene, but overlapping pZL1 clones #10 and #17 together encompassed the entire gene. The nucleotide sequence and deduced amino acid sequence are shown in FIG. 2. Sequence analysis of the cloned insert revealed a coding sequence of 2645 bp (excluding the stop codon) encoding a protein of 811 amino acids. Clone 10 contained nucleotides 390-2906 of SEQ ID NO:5 encoding amino acids 59-811 of SEQ ID NO:6, while clone 17 contained nucleotides 161-1749 of SEQ ID NO:5 encoding amino acids 1-459 of SEQ ID NO:6. The coding sequence is punctuated by four introns of 54 bp, 63 bp, 49, and 46 bp. The G+C content of the coding sequence (including introns) is 47.3%. The predicted RDHD polypeptide has a molecular mass of 99.2 kDa and an isoelectric point of 8.90. Using the Signal P software program (Nielsen et al., 1997, *Protein Engineering* 10:1-6), no signal peptide was predicted (Y<0.037).

A comparative alignment of the *Aspergillus oryzae* RDHD protein sequence with other sequences using the Clustal W algorithm in the Megalign program of DNASTAR, showed that the deduced amino acid sequence of the *Aspergillus oryzae* RDHD protein shares 74% identity with the deduced amino acid sequence of the MUS-25 protein of *Neurospora crassa* (accession number Q9P978).

Clones 10 and 17 were deposited as *E. coli* pZL1rdhD17 (NRRL B-30505) and *E. coli* pZL1rdhD10 (NRRL B-30506) on Jul. 27, 2001, with the Agricultural Research Service Patent Culture Collection, Northern Regional Research Center, 1815 University Street, Peoria, Ill.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
| --- | --- | --- |
| *E. coli* pZL1rdhA13 | NRRL B-30503 | Jul. 27, 2001 |
| *E. coli* pZL1rdhB6 | NRRL B-30504 | Jul. 27, 2001 |
| *E. coli* pZL1rdhD17 | NRRL B-30505 | Jul. 27, 2001 |
| *E. coli* pZL1rdhD10 | NRRL B-30506 | Jul. 27, 2001 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent a substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for increasing the homologous recombination of a nucleic acid sequence in a population of filamentous fungal host cells, the method comprising:
   (a) introducing into the population of the filamentous fungal host cells the nucleic acid sequence which comprises one or more regions which are homologous with one or more genomic regions of the filamentous fungal host cells and introducing a second nucleic acid sequence comprising expression control sequences directing expression of a nucleic acid sequence encoding a filamentous fungal recombination protein, wherein (i) the recombination protein promotes the recombination of the one or more regions with the corresponding homologous regions in the genome of the filamentous fungal host cell to incorporate the nucleic acid sequence therein by homologous recombination, and (ii) the number of host cells comprising the incorporated nucleic acid sequence in the population of the filamentous fungal host cells is increased at least 20% compared to the same population of filamentous fungal host cells without the second nucleic acid sequence; and
   (b) isolating from the population of the filamentous fungal host cells a filamentous fungal cell comprising the incorporated nucleic acid sequence;
   wherein the second nucleic acid sequence encoding the recombination protein is selected from the group consisting of: (1) a nucleic acid sequence encoding a recombination protein comprising or consisting of the amino acid sequence of SEQ ID NO: 2; and (2) a nucleic acid sequence comprising the nucleotide sequence of SEQ ID NO: 1, wherein the nucleic acid sequence encodes the recombination protein.

2. The method of claim 1, wherein the recombination protein comprises or consists of the amino acid sequence of SEQ ID NO: 2.

3. The method of claim 1, wherein the nucleic acid sequence further comprises (a) a gene that encodes a polypeptide or an RNA; (b) a gene disrupted with a third nucleic acid sequence; (c) a partially deleted gene; (d) a regulatory control sequence; or (e) a recombinant version of a gene native or foreign to the filamentous fungal host cell.

4. A method for producing a polypeptide in a filamentous fungal cell, the method comprising:
   (a) cultivating the filamentous fungal cell in a medium suitable for production of the polypeptide, wherein the filamentous fungal cell was obtained from a population of filamentous fungal cells produced by (a) introducing into the population of the filamentous fungal host cells a first nucleic acid sequence comprising expression control sequences directing expression of a nucleic acid sequence encoding a filamentous fungal recombination protein and a second nucleic acid sequence encoding the polypeptide or comprising a regulatory control sequence involved in the expression of a sequence in the genome of the filamentous fungal cell encoding the polypeptide and further comprising one or more regions which are homologous with one or more genomic regions of the filamentous fungal host cell, wherein (i) the recombination protein promotes the recombination of the one or more regions with the corresponding homologous regions in the genome of the filamentous fungal host cell to incorporate the second nucleic acid sequence therein by homologous recombination, and (ii) the number of host cells comprising the incorporated second nucleic acid sequence in the population of the filamentous fungal host cells is increased at least 20% compared to the same population of filamentous fungal host cells without the first nucleic acid sequence; and (b) isolating from the population of filamentous fungal host cells a filamentous fungal cell comprising the incorporated first nucleic acid sequence; and
   (b) recovering the polypeptide from the cultivation medium;
   wherein the first nucleic acid sequence encoding the recombination protein is selected from the group consisting of: (1) a nucleic acid sequence encoding a recombination protein comprising or consisting of the amino acid sequence of SEQ ID NO: 2; and (2) a nucleic acid sequence comprising the nucleotide sequence of SEQ ID NO: 1, wherein the nucleic acid sequence encodes the recombination protein.

5. The method of claim 4, wherein the recombination protein comprises or consists of the amino acid sequence of SEQ ID NO: 2.

6. The method of claim 4, wherein the second nucleic acid sequence further comprises (a) a gene, which encodes a polypeptide or an RNA; (b) a gene disrupted with a third nucleic acid sequence; (c) a partially deleted gene; (d) a regulatory control sequence; or (e) a recombinant version of a gene native or foreign to the filamentous fungal host cell.

7. A method for deleting or disrupting a gene in a filamentous fungal cell, the method comprising:
   (A) wherein the filamentous fungal cell is obtained from a population of filamentous fungal cells produced by introducing into the population of the filamentous fungal host cells a first nucleic acid sequence comprising expression control sequences directing expression of a nucleic acid sequence encoding a filamentous fungal recombination protein and a second nucleic acid sequence comprising one or more regions which are homologous with one or more genomic regions of the filamentous fungal host cell, wherein (i) the recombination protein promotes the recombination of the one or more regions with the corresponding homologous regions in the genome of the filamentous fungal host cell to incorporate the second nucleic acid sequence therein by homologous recombination to delete or disrupt the gene in the filamentous fungal cell, and (ii) the number of host cells comprising the incorporated second nucleic acid sequence in the population of the filamentous fungal host cells is increased at least 20% compared to the same population of filamentous fungal host cells without the first nucleic acid; and (B) isolating from the population of filamentous fungal cells a filamentous fungal cell comprising the deleted or disrupted gene;

wherein the first nucleic acid sequence encoding the recombination protein is selected from the group consisting of: (1) a nucleic acid sequence encoding a recombination protein comprising or consisting of the amino acid sequence of SEQ ID NO: 2; and (2) a nucleic acid sequence comprising the nucleotide sequence of SEQ ID NO: 1, wherein the nucleic acid sequence encodes the recombination protein.

8. The method of claim 7, wherein the recombination protein comprises or consists of the amino acid sequence of SEQ ID NO: 2.

9. The method of claim 7, wherein the second nucleic acid sequence further comprises (a) a gene disrupted with a third nucleic acid sequence; (b) a partially deleted gene; (c) a DNA fragment; or (d) a selectable marker gene.

* * * * *

SEQUENCE LISTING

```
<160> NUMBER OF SEQ ID NOS: 34

<210> SEQ ID NO 1
<211> LENGTH: 2032
<212> TYPE: DNA
<213> ORGANISM: A. oryzae

<400> SEQUENCE: 1
ttctcggact ggatgaagca agatgcaacg aagcaagctc atgatctgac attagggccc      60
ctctcatgtt tccttgcatt attgttccaa tatagcgttg cgtaattgta ggcttacctc     120
ttaaggcagc agcctgatgt gcctggaaca cgtgacctcg tgacagcctc gacgcgtcca     180
gaacctcaac aaattgttta tcgccgtaga gtcatacgcc attttgccac atcgaccgac     240
ttacgaattt taaataagac ttctattgtt tccaaactgg tgactacaaa gcagcctttg     300
gggtattcgt ccgataagaa acaatcctag cgaagaattc atccacagtt acaatagaac     360
gcgtcctgtc gcgtcgagta ggctgtgtgc aagaccagta gcagttgctt gattactctt     420
ggggctggct agggagacac tttacttgcc tacctgattg aaaatgacgg cggatatgga     480
tactcagaat gaatacgatg atagtggact tcccgggcct ggagcgccca cgccactttc     540
agctttagaa gtgaggaatc tctactgtcc acacaataca atattacaag cttgatttag     600
tagtaaaagc cccttcagt gacttgtact gaccattgac tcgatagggt gttgcgggat      660
taacgggaag agatatcaaa ttgtttgtcg atgccggcta tcacactgtc gaatcaattg     720
cgtatacgta cgtctttcct cttgaatgtt taaacgaact tgctgcagca ccaaacttgg     780
agagcttaag gagatgctga cattggcatt ggtggtacat catagaccga aacgtttact     840
ggaacaaatc aaaggtatat cggagcagaa ggccaccaag gttttggttg aaggttagtc     900
acctcaactc atggagctca accgtctgta aggattcgtg ctgattatac ctgataaata     960
gctgccaagc ttgtgccaat gggtttcacg actgcaacag aaatgcatgc acgtcgaagt    1020
gagctcatat cgatcacgac aggatccaag caactagata ctctcctagg cggtggtata    1080
gaaacgggat ctattaccga gatattcgga gaattcagga caggtaaaag tcaaatttgc    1140
catacgcttg cagtgacttg ccagctgcca ttcgacatgg gtggtgggga agggaagtgt    1200
ctttatattg atactgaagg gacatttcga ccggtccgtc tgttggcagt tgctcaaaga    1260
tacggacttg ttggcgaaga ggtactcgat aatgtggcct atgcccgcgc ttataactcg    1320
gatcaccagc tccagctgct gaaccaggcg tctcaaatga tgtgcgaaac tcgtttctca    1380
cttcttgtcg tcgactctgc tacagcgcta tatcggacag attttaacgg ccgtggtgaa    1440
ctatcgactc gacaaacaca tctcgctaaa ttcatgcgta ccttgcagcg cttggcggat    1500
gaatttggta ttgccgtcgt catcaccaac caggtcgtcg cccaggtcga cggcggtccg    1560
agtgcaatgt tcaacccaga ccccaagaag ccaatcggtg gaaacattat cgcacacgcc    1620
agcacgacca ggctgagtct gaaaaagggg agaggagaga cccgagtgtg caagatctat    1680
gacagtccct gtctgcccga gagtgactgt cttttgcta tcaatgaaga tggtattggg      1740
```

-continued

```
gatcctagcc ccaaggactt ggaaaacaac tgaggagcga tgaagctgta ttaattactt    1800
acgataccac gatcggtata tgattttact tggtttgttc tttagtacat attgtttagt    1860
atcttgattt tgatagcata cggtgtttgt ggtattgtgc tagattttat gtgctaattg    1920
agataaaagt tgatcaataa aaaagaact atgacttgta tatacaaaga acgtatggtc    1980
ttctaataat atctatttcg aacgatttgc tcttctgtcc ttccatcaaa tt            2032
```

<210> SEQ ID NO 2
<211> LENGTH: 315
<212> TYPE: PRT
<213> ORGANISM: A. oryzae

<400> SEQUENCE: 2

```
Met Thr Ala Asp Met Asp Thr Gln Asn Glu Tyr Asp Asp Ser Gly Leu
1               5                   10                  15

Pro Gly Pro Gly Ala Pro Thr Pro Leu Ser Ala Leu Glu Gly Val Ala
            20                  25                  30

Gly Leu Thr Gly Arg Asp Ile Lys Leu Phe Val Asp Ala Gly Tyr His
        35                  40                  45

Thr Val Glu Ser Ile Ala Tyr Thr Pro Lys Arg Leu Leu Glu Gln Ile
    50                  55                  60

Lys Gly Ile Ser Glu Gln Lys Ala Thr Lys Val Leu Val Glu Ala Ala
65                  70                  75                  80

Lys Leu Val Pro Met Gly Phe Thr Ala Thr Glu Met His Ala Arg
                85                  90                  95

Arg Ser Glu Leu Ile Ser Ile Thr Thr Gly Ser Lys Gln Leu Asp Thr
            100                 105                 110

Leu Leu Gly Gly Gly Ile Glu Thr Gly Ser Ile Thr Glu Ile Phe Gly
        115                 120                 125

Glu Phe Arg Thr Gly Lys Ser Gln Ile Cys His Thr Leu Ala Val Thr
130                 135                 140

Cys Gln Leu Pro Phe Asp Met Gly Gly Gly Glu Gly Lys Cys Leu Tyr
145                 150                 155                 160

Ile Asp Thr Glu Gly Thr Phe Arg Pro Val Arg Leu Leu Ala Val Ala
                165                 170                 175

Gln Arg Tyr Gly Leu Val Gly Glu Glu Val Leu Asp Asn Val Ala Tyr
            180                 185                 190

Ala Arg Ala Tyr Asn Ser Asp His Gln Leu Gln Leu Leu Asn Gln Ala
        195                 200                 205

Ser Gln Met Met Cys Glu Thr Arg Phe Ser Leu Leu Val Val Asp Ser
    210                 215                 220

Ala Glu Phe Gly Ile Ala Val Val Ile Thr Asn Gln Val Val Ala Gln
225                 230                 235                 240

Val Asp Gly Gly Pro Ser Ala Met Phe Asn Pro Asp Pro Lys Lys Pro
                245                 250                 255

Ile Gly Gly Asn Ile Ile Ala His Ala Ser Thr Thr Arg Leu Ser Leu
            260                 265                 270

Lys Lys Gly Arg Gly Glu Thr Arg Val Cys Lys Ile Tyr Asp Ser Pro
        275                 280                 285

Cys Leu Pro Glu Ser Asp Cys Leu Phe Ala Ile Asn Glu Asp Gly Ile
    290                 295                 300

Gly Asp Pro Ser Pro Lys Asp Leu Glu Asn Asn
305                 310                 315
```

<210> SEQ ID NO 3
<211> LENGTH: 2500
<212> TYPE: DNA
<213> ORGANISM: A. oryzae

<400> SEQUENCE: 3

| | | | | | |
|---|---|---|---|---|---|
| gtggtatcgc | gactgtcgga | ttccgtcacg | cgtcgagcag | ctcagttgac | ctctgtctat | 60 |
| cttcattacc | ccccactgtg | tacgccacgc | gcatcggtgt | ataccaatga | tacccttct | 120 |
| taactagtgt | aacatttata | tatcttttaa | taatgcccgc | gtgagccacc | ccagtgtgct | 180 |
| acgctaccgc | tgctattaat | cccgatctaa | gctaacgcgt | cttagtgttg | gcgaccaaca | 240 |
| tcgaggcaat | ccgacatgca | tcatgatgcc | caacacgaca | gacactacat | cagcaaaccc | 300 |
| ctttgaggaa | cgtcctcgcc | gcatgaatga | gtatacagct | cgggagatcg | ccacactgca | 360 |
| agcacggctc | gataagaaat | taggccccga | atacatctcc | tctaggccag | cgccgcggg | 420 |
| acagagagtc | cattatctgg | ctgcagacaa | atgcattaac | ctagccaacg | aggtctttgg | 480 |
| tttcaatggg | tggtcaagtt | cgatacaaca | aattcagatc | gatttcgtat | gttctattga | 540 |
| taggagcata | tctatgttgc | gtgtgcccga | gatcggacag | ctgataaatc | cctcgttgta | 600 |
| acaggttgac | gagagcccaa | atacggggaa | gattagcttg | ggcttgtcag | ttgtagtgag | 660 |
| ggtgactcta | aaggatggga | cctaccatga | ggtatacttt | tgcgtgaatg | atatgctccg | 720 |
| atgtgcccaa | acgctaacca | ctttggacga | cgttaggata | tcgggtacgg | ccacattgag | 780 |
| aactgtaaag | ggaaagctgc | ggctttcgaa | aaagcaaaga | aagaaggaac | cacagatgcc | 840 |
| ctaaagcgta | cattgaggaa | cttcggcaac | gtcctgggca | attgcattta | tgataaggat | 900 |
| tacgtatcga | aagtgacgaa | agtgaagaca | gcgcctgtat | gtgtttctac | ggcatattac | 960 |
| tcgactagac | tcaggtacta | acatgctccc | aggcaagatg | ggacgtggat | gaccttcacc | 1020 |
| gacaccctga | tttcgcaccc | atcaagaaag | aaccagttca | acagaagccg | atgcaggagg | 1080 |
| atgatgatct | ccctcctcgc | ccgactgatg | cgggaaagaa | caacagtaac | tcagccgata | 1140 |
| ctgcctttga | tgctgatgga | gagttcggaa | gtacgtaacg | ataaatcaag | ctaccttgca | 1200 |
| tgcatttcac | taacgatcgc | aggtgattta | tttgacgaag | cggactttgg | agtcgccgca | 1260 |
| actggaaacc | cagatgaaat | agtaatagac | ccagatacc | aaagatttca | gcagccacca | 1320 |
| acacctctga | accgtcaaaa | tggcccagcc | ccgtacaggg | gccctcaaca | gcataacccc | 1380 |
| ttagccgctg | caagaccca | ttccgccatt | gccacaccat | ccaaaccaga | aagaccgccg | 1440 |
| aaccaggcag | ctgccgctag | acagatacca | cctcctgctc | tgaatggcag | accaaaccct | 1500 |
| gctgcacccg | cccacaaccc | gcaacacaac | cttccaagcg | gaagaatacc | accagctcaa | 1560 |
| ccaagaccta | atcaagacac | agccatgccc | ggtgcaagtg | gtcagatgcc | catcaaacgg | 1620 |
| gaacaagttc | ctaatcccaa | cgaccccgga | acccaggaca | tgctcccacc | aggaagctca | 1680 |
| ccgatgccat | ctgcctcatt | cttctcagct | cgagcagtcg | atctcctacg | tgacaaccca | 1740 |
| caagcaaacg | cagccccggc | attcgacccc | catgcagaaa | gcccatccat | ccgcaagaca | 1800 |
| gctggcgtcg | accacagtaa | gagcgtcccg | atttccaaac | ccatgcttgc | cagcgtatcc | 1860 |
| cccgccgcca | acaatacccg | tgacttcgtc | aacccttctc | aagatatgca | tcggaaaatc | 1920 |
| ggcgctccta | gcggaatagg | cagtcccatg | aatcgaggcc | agacaacctc | atcttaccgc | 1980 |
| ccattaacaa | gaccgaacat | cgaccccaag | aatgctgtga | atactacagc | tgcaaaccgg | 2040 |
| ggcgtcgggc | cacaaaatct | aaatgggaaa | cgacctcccc | taagtgatgt | gactaatgca | 2100 |
| tccacttag | gcggcagcgg | gcctgctccc | attggtggtg | cgatagaccc | taagaggcca | 2160 |
| aaaatcaacg | acgggcctct | tccacaccaa | cagcaacaac | atccgcaata | ggactcctag | 2220 |

-continued

```
cggatttagt atagttacac ggcaacataa ataatagcca tgcttacggg gagatcgtcc   2280
actcattgca tcgttagagg tcatctcatc ggtagttcaa gacatggcgt tcaggattgg   2340
ggtacgggta aaggagctcc gggttaaatg taatgaatgt tcttgatgaa tgttattttt   2400
gttatattct cttcactcca gcttaaagca tccaagacgt gcctccttag gcagttgtgt   2460
gactggattg tctacggaca ctacacagct tgtactatac                         2500
```

<210> SEQ ID NO 4
<211> LENGTH: 565
<212> TYPE: PRT
<213> ORGANISM: A. oryzae

<400> SEQUENCE: 4

```
Met Met Pro Asn Thr Thr Asp Thr Thr Ser Ala Asn Pro Phe Glu Glu
1               5                   10                  15

Arg Pro Arg Arg Met Asn Glu Tyr Thr Ala Arg Glu Ile Ala Thr Leu
                20                  25                  30

Gln Ala Arg Leu Asp Lys Lys Leu Gly Pro Glu Tyr Ile Ser Ser Arg
            35                  40                  45

Pro Gly Ala Ala Gly Gln Arg Val His Tyr Leu Ala Ala Asp Lys Cys
        50                  55                  60

Ile Asn Leu Ala Asn Glu Val Phe Gly Phe Asn Gly Trp Ser Ser Ser
65                  70                  75                  80

Ile Gln Gln Ile Gln Ile Asp Phe Val Asp Glu Ser Pro Asn Thr Gly
                85                  90                  95

Lys Ile Ser Leu Gly Leu Ser Val Val Arg Val Thr Leu Lys Asp
                100                 105                 110

Gly Thr Tyr His Glu Asp Ile Gly Tyr Gly His Ile Glu Asn Cys Lys
            115                 120                 125

Gly Lys Ala Ala Ala Phe Glu Lys Ala Lys Lys Glu Gly Thr Thr Asp
        130                 135                 140

Ala Leu Lys Arg Thr Leu Arg Asn Phe Gly Asn Val Leu Gly Asn Cys
145                 150                 155                 160

Ile Tyr Asp Lys Asp Tyr Val Ser Lys Val Thr Lys Val Lys Thr Ala
                165                 170                 175

Pro Ala Arg Trp Asp Val Asp Asp Leu His Arg His Pro Asp Phe Ala
            180                 185                 190

Pro Ile Lys Lys Glu Pro Val Gln Gln Lys Pro Met Gln Glu Asp Asp
        195                 200                 205

Asp Leu Pro Pro Arg Pro Thr Asp Ala Gly Lys Asn Asn Ser Asn Ser
210                 215                 220

Ala Asp Thr Ala Phe Asp Ala Asp Gly Glu Phe Gly Ser Asp Leu Phe
225                 230                 235                 240

Asp Glu Ala Asp Phe Gly Val Ala Ala Thr Gly Asn Pro Asp Glu Ile
                245                 250                 255

Val Ile Asp Pro Asp Thr Gln Arg Phe Gln Gln Pro Thr Pro Leu
            260                 265                 270

Asn Arg Gln Asn Gly Pro Ala Pro Tyr Arg Gly Pro Gln Gln His Asn
        275                 280                 285

Pro Leu Ala Ala Ala Arg Pro His Ser Ala Ile Ala Thr Pro Ser Lys
290                 295                 300

Pro Glu Arg Pro Pro Asn Gln Ala Ala Ala Arg Gln Ile Pro Pro
                305                 310                 315                 320

Pro Ala Leu Asn Gly Arg Pro Asn Pro Ala Ala Pro Ala His Asn Pro
            325                 330                 335
```

```
Gln His Asn Leu Pro Ser Gly Arg Ile Pro Ala Gln Pro Arg Pro
            340                 345                 350

Asn Gln Asp Thr Ala Met Pro Gly Ala Ser Gly Gln Met Pro Ile Lys
        355                 360                 365

Arg Glu Gln Val Pro Asn Pro Asn Asp Pro Gly Thr Gln Asp Met Leu
    370                 375                 380

Pro Pro Gly Ser Ser Pro Met Pro Ser Ala Ser Phe Phe Ser Ala Arg
385                 390                 395                 400

Ala Val Asp Leu Leu Arg Asp Asn Pro Gln Ala Asn Ala Ala Pro Ala
                405                 410                 415

Phe Asp Pro His Ala Glu Ser Pro Ser Ile Arg Lys Thr Ala Gly Val
                420                 425                 430

Asp His Ser Lys Ser Val Pro Ile Ser Lys Pro Met Leu Ala Ser Val
            435                 440                 445

Ser Pro Ala Ala Asn Asn Thr Arg Asp Phe Val Asn Pro Ser Gln Asp
        450                 455                 460

Met His Arg Lys Ile Gly Ala Pro Ser Gly Ile Gly Ser Pro Met Asn
465                 470                 475                 480

Arg Gly Gln Thr Thr Ser Ser Tyr Arg Pro Leu Thr Arg Pro Asn Ile
                485                 490                 495

Asp Pro Lys Asn Ala Val Asn Thr Thr Ala Ala Asn Arg Gly Val Gly
            500                 505                 510

Pro Gln Asn Leu Asn Gly Lys Arg Pro Pro Leu Ser Asp Val Thr Asn
        515                 520                 525

Ala Ser Thr Leu Gly Gly Ser Gly Pro Ala Pro Ile Gly Gly Ala Ile
    530                 535                 540

Asp Pro Lys Arg Pro Lys Ile Asn Asp Gly Pro Leu Pro His Gln Gln
545                 550                 555                 560

Gln Gln His Pro Gln
            565

<210> SEQ ID NO 5
<211> LENGTH: 2981
<212> TYPE: DNA
<213> ORGANISM: A. oryzae
<220> FEATURE:
<221> NAME/KEY: misc_feature
<222> LOCATION: (2932)..(2932)
<223> OTHER INFORMATION: n= a,c,g, or t

<400> SEQUENCE: 5
gacagcgtga tactttggtg tttagacggc cacagggaaa cgcgccaaga tgtggcaacg        60
cgttgttcat gactctatgg aactgacatt gactgccagg catcagccca cctattactg       120
cgtgaaatag aaaggctttc tagatagcac cgctaccttt aatgtaagga aatatattaat      180 tctgttctct catgctataa atcgctaact tctcaaggta tcgaccacga ccgagtgtaa       240
gggaagatgg cggaagcaca ccgtcatcca aaaacctcca aaccccgtcc tcaaagtcca       300
ttgaccgcct atcaaaacca ttcaaatgcc ctggatctgc tacacccaca cggacatcgg       360
ataaacctgc gaggaaacga agaaaggtga attatgcggg ggctgatgaa actgtggacg       420
ataatagtga aaagccatac accaacgagg aacgtttagc actcgccacc agagatgtga       480
acaggttccc tgtgttcaaa cctaaagata aagagacaac cttcaaacaa cgattcaaga       540
tacctttaat caacaaggcg gttgacagct acaatggcgc tagggcggcg ccaaccttgg       600
ggatgcgaca aggtgctaca tttgtcgtga aacctctaca tgatcctagc ggagaatttg       660
```

```
cgatagtgct gtatgatccg actgtcgatg atgccgatga aacagtgaa  acgaagttgc   720
cggaagatgg aaaacccgaa gaacaacaac ccaagttgga cgctcccctt gtacacaaga   780
gcttagcaga catacttggt cttaagaaga aagttgaaac tggtccaagg gttccagtcg   840
tgatagaccc aaggttggca aaggttctac gcccacatca aattgaaggt gtaaaggtaa   900
catgactgtt ccaatcaatg ctctcctgcg atattagact aacgataact gttttctagt   960
ttttataccg ctgcacaacc ggaatggtcg ataagaacgc acacggctgt ataatggcgg  1020
atggaatggg actagggaaa acagtatggc cgacagaccc ttcaaaacac taaccccggc  1080
tgacggcgat agcttcaatg catctcattg atgtggacat tgctcaagca gtctcctgag  1140
gcaggcaaga cccttatcca gaagtgtatc attgcttgtc cttcaagttt ggttggcaac  1200
tgggccaatg agctaggtag gtagtgcgcc ctggatgttt taacacctgc taacaaccac  1260
agtgaaatgg ctaggtaaag atgccatcac tccttttgcg gtggatggca aagcttcgaa  1320
gacagaactc acatctcaga tcaagcaatg ggctattgct tccggtcgcg ccgttgtgag  1380
acctgtgctc attgtgtcct acgaaacgct caggatgtat gttgaagcat tgaaggatag  1440
ccccataggg ctacttcttt gcgatgaagg tcatcggctt aaaaataagg atagtttaac  1500
atggactgca ctcaacagtc tgaatgtgca acgtcgtgtt atcttgtcag gaaccctat   1560
tcaaaatgat ctttcggaat atttcgccct gctcaacttc gccaacccag atttattagg  1620
gtcgcagaat gaatttcgga aaaggttcga attgcctatc ctcagaggaa gggatgccgc  1680
aggatcggac gaagacaaaa agaaaggcga tgaatgtcta gctgagctct caaccatcgt  1740
caacaaattc attatccgcc gaacaaatga tatattgacg aaatacttgc cagtcaagta  1800
tgagcatgtt gtcttttgca atttgtctca attccaactc gacctttata accacttcat  1860
tcagagccca gaaattagga gcttgctcag gggcaaagga agccagccgc ttaaggcaat  1920
tggccttttg aaaaagcttt gcaaccatcc tgatctactt aaccttttcca ccgaccttcc  1980
aggatgcgaa tttgcatttc cagaagatta cgtgccacct gaggcaagag ggcgtgaccg  2040
cgatatcaag tcttggtact cggggaaaat gatggttttg gatcgaatgc tagcacgtat  2100
acgccaggac acaaatgaca aaattgttct cattagtaat tacacccaga cacttgacct  2160
gttcgaaaag ctatgcagat cgagggggta tggctcgttg agactggacg gtactatgaa  2220
tgtgaataag cggcaaaagc tcgtcgacaa attcaacaac cctgacgggg aagaatttgt  2280
atttctcctc agcagcaagg ccggtggatg tggcctcaat ctaataggcg ccaatcgtct  2340
cgtgctgttt gacccagatt ggaacccagc tgctgatcaa caagcattgg cacgagtttg  2400
gcgtgatggt cagaagaaag actgtttcgt gtaccgattt atcgcgaccg gctcaattga  2460
ggagaagatc ttccaacggc agtctcataa gcaatcattg tcctcatgcg ttgtggattc  2520
agcggaagat gttgagcggc attttttcttt ggagtctctc cgcgaactat tccaattcaa  2580
accggaaacc cgaagtgaca cacatgacac cttcaagtgc aagagatgca gaccggatgg  2640
agcgcaattc atcaaggcgc aggctatgtt gtatggcgat accagcacct ggaatcactt  2700
tgttaatgat ggcgagaagg gtgcccttag caagatccag gacctgctga tacgacagga  2760
gaccggggag agagatgtgt ctgcggtatt ccagtatata agtcactgat ctaattctta  2820
caagcgtcgt gtttttacact gtctatatgt tcaaagcagt tgatgctacg gcaatcatga  2880
gttggcacaa ttctgggctg tcagtgcagc tatttacatt tggtagctag gnatatcatg  2940
cattcatgct tttgctatca taggctacat taggtctatg g                     2981
```

```
<210> SEQ ID NO 6
<211> LENGTH: 811
<212> TYPE: PRT
<213> ORGANISM: A. oryzae

<400> SEQUENCE: 6

Met Tyr Arg Pro Arg Pro Ser Val Arg Glu Asp Gly Gly Ser Thr Pro
1               5                   10                  15

Ser Ser Lys Asn Leu Gln Thr Pro Ser Ser Lys Ser Ile Asp Arg Leu
            20                  25                  30

Ser Lys Pro Phe Lys Cys Pro Gly Ser Ala Thr Pro Thr Arg Thr Ser
        35                  40                  45

Asp Lys Pro Ala Arg Lys Arg Arg Lys Val Asn Tyr Ala Gly Ala Asp
    50                  55                  60

Glu Thr Val Asp Asp Asn Ser Glu Lys Pro Tyr Thr Asn Glu Glu Arg
65                  70                  75                  80

Leu Ala Leu Ala Thr Arg Asp Val Asn Arg Phe Pro Val Phe Lys Pro
                85                  90                  95

Lys Asp Lys Glu Thr Thr Phe Lys Gln Arg Phe Lys Ile Pro Leu Ile
            100                 105                 110

Asn Lys Ala Val Asp Ser Tyr Asn Gly Ala Arg Ala Ala Pro Thr Leu
        115                 120                 125

Gly Met Arg Gln Gly Ala Thr Phe Val Val Lys Pro Leu His Asp Pro
    130                 135                 140

Ser Gly Glu Phe Ala Ile Val Leu Tyr Asp Pro Thr Val Asp Asp Ala
145                 150                 155                 160

Asp Glu Asn Ser Glu Thr Lys Leu Pro Glu Asp Gly Lys Pro Glu Glu
                165                 170                 175

Gln Gln Pro Lys Leu Asp Ala Pro Leu Val His Lys Ser Leu Ala Asp
            180                 185                 190

Ile Leu Gly Leu Lys Lys Lys Val Glu Thr Gly Pro Arg Val Pro Val
        195                 200                 205

Val Ile Asp Pro Arg Leu Ala Lys Val Leu Arg Pro His Gln Ile Glu
    210                 215                 220

Gly Val Lys Phe Leu Tyr Arg Cys Thr Thr Gly Met Val Asp Lys Asn
225                 230                 235                 240

Ala His Gly Cys Ile Met Ala Asp Gly Met Gly Leu Gly Lys Thr Leu
                245                 250                 255

Gln Cys Ile Ser Leu Met Trp Thr Leu Leu Lys Gln Ser Pro Glu Ala
            260                 265                 270

Gly Lys Thr Leu Ile Gln Lys Cys Ile Ile Ala Cys Pro Ser Ser Leu
        275                 280                 285

Val Gly Asn Trp Ala Asn Glu Leu Val Lys Trp Leu Gly Lys Asp Ala
    290                 295                 300

Ile Thr Pro Phe Ala Val Asp Gly Lys Ala Ser Lys Thr Glu Leu Thr
305                 310                 315                 320

Ser Gln Ile Lys Gln Trp Ala Ile Ala Ser Gly Arg Ala Val Val Arg
                325                 330                 335

Pro Val Leu Ile Val Ser Tyr Glu Thr Leu Arg Met Tyr Val Glu Ala
            340                 345                 350

Leu Lys Asp Ser Pro Ile Gly Leu Leu Leu Cys Asp Glu Gly His Arg
        355                 360                 365
```

```
Leu Lys Asn Lys Asp Ser Leu Thr Trp Thr Ala Leu Asn Ser Leu Asn
        370                 375                 380

Val Gln Arg Arg Val Ile Leu Ser Gly Thr Pro Ile Gln Asn Asp Leu
385                 390                 395                 400

Ser Glu Tyr Phe Ala Leu Leu Asn Phe Ala Asn Pro Asp Leu Leu Gly
                405                 410                 415

Ser Gln Asn Glu Phe Arg Lys Arg Phe Glu Leu Pro Ile Leu Arg Gly
            420                 425                 430

Arg Asp Ala Ala Gly Ser Asp Glu Asp Lys Lys Gly Asp Glu Cys
            435                 440                 445

Leu Ala Glu Leu Ser Thr Ile Val Asn Lys Phe Ile Arg Arg Thr
        450                 455                 460

Asn Asp Ile Leu Thr Lys Tyr Leu Pro Val Lys Tyr Glu His Val Val
465                 470                 475                 480

Phe Cys Asn Leu Ser Gln Phe Gln Leu Asp Leu Tyr Asn His Phe Ile
                485                 490                 495

Gln Ser Pro Glu Ile Arg Ser Leu Leu Arg Gly Lys Gly Ser Gln Pro
            500                 505                 510

Leu Lys Ala Ile Gly Leu Leu Lys Lys Leu Cys Asn His Pro Asp Leu
        515                 520                 525

Leu Asn Leu Ser Thr Asp Leu Pro Gly Cys Glu Phe Ala Phe Pro Glu
530                 535                 540

Asp Tyr Val Pro Pro Glu Ala Arg Gly Arg Asp Arg Asp Ile Lys Ser
545                 550                 555                 560

Trp Tyr Ser Gly Lys Met Met Val Leu Asp Arg Met Leu Ala Arg Ile
                565                 570                 575

Arg Gln Asp Thr Asn Asp Lys Ile Val Leu Ile Ser Asn Tyr Thr Gln
            580                 585                 590

Thr Leu Asp Leu Phe Glu Lys Leu Cys Arg Ser Arg Gly Tyr Gly Ser
        595                 600                 605

Leu Arg Leu Asp Gly Thr Met Asn Val Asn Lys Arg Gln Lys Leu Val
        610                 615                 620

Asp Lys Phe Asn Asn Pro Asp Gly Glu Glu Phe Val Phe Leu Leu Ser
625                 630                 635                 640

Ser Lys Ala Gly Gly Cys Gly Leu Asn Leu Ile Gly Ala Asn Arg Leu
                645                 650                 655

Val Leu Phe Asp Pro Asp Trp Asn Pro Ala Ala Asp Gln Gln Ala Leu
                660                 665                 670

Ala Arg Val Trp Arg Asp Gly Gln Lys Lys Asp Cys Phe Val Tyr Arg
            675                 680                 685

Phe Ile Ala Thr Gly Ser Ile Glu Glu Lys Ile Phe Gln Arg Gln Ser
        690                 695                 700

His Lys Gln Ser Leu Ser Ser Cys Val Val Asp Ser Ala Glu Asp Val
705                 710                 715                 720

Glu Arg His Phe Ser Leu Glu Ser Leu Arg Glu Leu Phe Gln Phe Lys
                725                 730                 735

Pro Glu Thr Arg Ser Asp Thr His Asp Thr Phe Lys Cys Lys Arg Cys
            740                 745                 750

Arg Pro Asp Gly Ala Gln Phe Ile Lys Ala Gln Ala Met Leu Tyr Gly
        755                 760                 765

Asp Thr Ser Thr Trp Asn His Phe Val Asn Asp Gly Glu Lys Gly Ala
770                 775                 780
```

-continued

Leu Ser Lys Ile Gln Asp Leu Leu Ile Arg Gln Glu Thr Gly Glu Arg
785                 790                 795                 800

Asp Val Ser Ala Val Phe Gln Tyr Ile Ser His
                805                 810

<210> SEQ ID NO 7
<211> LENGTH: 20
<212> TYPE: DNA
<213> ORGANISM: A. oryzae
<220> FEATURE:
<221> NAME/KEY: misc_feature
<222> LOCATION: (3)..(3)
<223> OTHER INFORMATION: y= c or t
<220> FEATURE:
<221> NAME/KEY: misc_feature
<222> LOCATION: (6)..(6)
<223> OTHER INFORMATION: y= c or t
<220> FEATURE:
<221> NAME/KEY: misc_feature
<222> LOCATION: (9)..(9)
<223> OTHER INFORMATION: n= inosine
<220> FEATURE:
<221> NAME/KEY: misc_feature
<222> LOCATION: (12)..(12)
<223> OTHER INFORMATION: n= inosine
<220> FEATURE:
<221> NAME/KEY: misc_feature
<222> LOCATION: (15)..(15)
<223> OTHER INFORMATION: y= c or t
<220> FEATURE:
<221> NAME/KEY: misc_feature
<222> LOCATION: (18)..(18)
<223> OTHER INFORMATION: n= a,c,g or t
<220> FEATURE:
<221> NAME/KEY: misc_feature
<222> LOCATION: (19)..(19)
<223> OTHER INFORMATION: m= a or c

<400> SEQUENCE: 7
gayaaygtng cntaygcnmg                                           20

<210> SEQ ID NO 8
<211> LENGTH: 20
<212> TYPE: DNA
<213> ORGANISM: A. oryzae
<220> FEATURE:
<221> NAME/KEY: misc_feature
<222> LOCATION: (3)..(3)
<223> OTHER INFORMATION: n= inosine
<220> FEATURE:
<221> NAME/KEY: misc_feature
<222> LOCATION: (6)..(6)
<223> OTHER INFORMATION: r= a or g
<220> FEATURE:
<221> NAME/KEY: misc_feature
<222> LOCATION: (9)..(9)
<223> OTHER INFORMATION: n= a,c, g or t
<220> FEATURE:
<221> NAME/KEY: misc_feature
<222> LOCATION: (12)..(12)
<223> OTHER INFORMATION: r= a or g
<220> FEATURE:
<221> NAME/KEY: misc_feature
<222> LOCATION: (15)..(15)
<223> OTHER INFORMATION: r= a or g

<400> SEQUENCE: 8
ttnggrtcng grttraacat                                           20

<210> SEQ ID NO 9
<211> LENGTH: 20
<212> TYPE: DNA
<213> ORGANISM: A. oryzae

```
<220> FEATURE:
<221> NAME/KEY: misc_feature
<222> LOCATION: (3)..(3)
<223> OTHER INFORMATION: y= c or t
<220> FEATURE:
<221> NAME/KEY: misc_feature
<222> LOCATION: (6)..(6)
<223> OTHER INFORMATION: n= inosine
<220> FEATURE:
<221> NAME/KEY: misc_feature
<222> LOCATION: (9)..(9)
<223> OTHER INFORMATION: n= inosine
<220> FEATURE:
<221> NAME/KEY: misc_feature
<222> LOCATION: (12)..(12)
<223> OTHER INFORMATION: n= a,c,g or t
<220> FEATURE:
<221> NAME/KEY: misc_feature
<222> LOCATION: (15)..(15)
<223> OTHER INFORMATION: y= c or t
<220> FEATURE:
<221> NAME/KEY: misc_feature
<222> LOCATION: (18)..(18)
<223> OTHER INFORMATION: r= a or g

<400> SEQUENCE: 9
acytgngcna cnacytgrtt                                              20

<210> SEQ ID NO 10
<211> LENGTH: 29
<212> TYPE: DNA
<213> ORGANISM: A. oryzae
<220> FEATURE:
<221> NAME/KEY: misc_feature
<222> LOCATION: (20)..(20)
<223> OTHER INFORMATION: y= c or t
<220> FEATURE:
<221> NAME/KEY: misc_feature
<222> LOCATION: (23)..(23)
<223> OTHER INFORMATION: y= c or t
<220> FEATURE:
<221> NAME/KEY: misc_feature
<222> LOCATION: (26)..(26)
<223> OTHER INFORMATION: n= a,c,g or t

<400> SEQUENCE: 10
cgaacgaagt cttcggttty aayggntgg                                    29

<210> SEQ ID NO 11
<211> LENGTH: 30
<212> TYPE: DNA
<213> ORGANISM: A. oryzae
<220> FEATURE:
<221> NAME/KEY: misc_feature
<222> LOCATION: (19)..(19)
<223> OTHER INFORMATION: n= a,c,g, or t
<220> FEATURE:
<221> NAME/KEY: misc_feature
<222> LOCATION: (22)..(22)
<223> OTHER INFORMATION: y= c or t
<220> FEATURE:
<221> NAME/KEY: misc_feature
<222> LOCATION: (25)..(25)
<223> OTHER INFORMATION: y= c or t
<220> FEATURE:
<221> NAME/KEY: misc_feature
<222> LOCATION: (28)..(28)
<223> OTHER INFORMATION: y= c or t

<400> SEQUENCE: 11
cttcatgccg tcggtagtnc cytcyttytt                                   30
```

```
<210> SEQ ID NO 12
<211> LENGTH: 42
<212> TYPE: DNA
<213> ORGANISM: A. oryzae

<400> SEQUENCE: 12
tatcaattct taattaagga tccaagcttg tttaaacaat tc                              42

<210> SEQ ID NO 13
<211> LENGTH: 40
<212> TYPE: DNA
<213> ORGANISM: A. oryzae

<400> SEQUENCE: 13
agttaacaat taattcctag gttcgaacaa atttgttaac                                 40

<210> SEQ ID NO 14
<211> LENGTH: 33
<212> TYPE: DNA
<213> ORGANISM: A. oryzae

<400> SEQUENCE: 14
gatacatgtt atggagatgt tctatcacac aag                                        33

<210> SEQ ID NO 15
<211> LENGTH: 29
<212> TYPE: DNA
<213> ORGANISM: A. oryzae

<400> SEQUENCE: 15
caggatcctg cagtattgac tactatggt                                             29

<210> SEQ ID NO 16
<211> LENGTH: 32
<212> TYPE: DNA
<213> ORGANISM: A. oryzae

<400> SEQUENCE: 16
ctgtttaaac tgcagggagg aactgaaaaa gg                                         32

<210> SEQ ID NO 17
<211> LENGTH: 31
<212> TYPE: DNA
<213> ORGANISM: A. oryzae

<400> SEQUENCE: 17
gttaagcttg cgaaacgcaa ataatgtgtt g                                          31

<210> SEQ ID NO 18
<211> LENGTH: 35
<212> TYPE: DNA
<213> ORGANISM: A. oryzae

<400> SEQUENCE: 18
gttacatgtc tccagaacga cgcccggcgg acatc                                      35

<210> SEQ ID NO 19
<211> LENGTH: 28
<212> TYPE: DNA
<213> ORGANISM: A. oryzae

<400> SEQUENCE: 19
tgaagcttca gatctcggtg acgggcag                                              28
```

```
<210> SEQ ID NO 20
<211> LENGTH: 33
<212> TYPE: DNA
<213> ORGANISM: A. oryzae

<400> SEQUENCE: 20
ggttaattaa ccggcaggga aggccaatga aag                                    33

<210> SEQ ID NO 21
<211> LENGTH: 39
<212> TYPE: DNA
<213> ORGANISM: A. oryzae

<400> SEQUENCE: 21
ccacgcgtat ttaaatgtcc gggatggata gcactgtgg                              39

<210> SEQ ID NO 22
<211> LENGTH: 37
<212> TYPE: DNA
<213> ORGANISM: A. oryzae

<400> SEQUENCE: 22
ggacgcgtgc ggccgcgtac caggagtacg tcgcagg                                37

<210> SEQ ID NO 23
<211> LENGTH: 28
<212> TYPE: DNA
<213> ORGANISM: A. oryzae

<400> SEQUENCE: 23
ggagatctgc agctgtgtac caatagac                                          28

<210> SEQ ID NO 24
<211> LENGTH: 25
<212> TYPE: DNA
<213> ORGANISM: A. oryzae

<400> SEQUENCE: 24
catttaaatg atgacggcgg atatg                                             25

<210> SEQ ID NO 25
<211> LENGTH: 27
<212> TYPE: DNA
<213> ORGANISM: A. oryzae

<400> SEQUENCE: 25
gttaattaat cagttgtttt ccaagtc                                           27

<210> SEQ ID NO 26
<211> LENGTH: 27
<212> TYPE: DNA
<213> ORGANISM: A. oryzae

<400> SEQUENCE: 26
agcggccgct cagttgtttt ccaagtc                                           27

<210> SEQ ID NO 27
<211> LENGTH: 28
<212> TYPE: DNA
<213> ORGANISM: A. oryzae

<400> SEQUENCE: 27
atttaaatga tgcccaacac gacagaca                                          28
```

```
<210> SEQ ID NO 28
<211> LENGTH: 28
<212> TYPE: DNA
<213> ORGANISM: A. oryzae

<400> SEQUENCE: 28
ttaattaact attgcggatg ttgttgct                                           28

<210> SEQ ID NO 29
<211> LENGTH: 27
<212> TYPE: DNA
<213> ORGANISM: A. oryzae

<400> SEQUENCE: 29
gcggccgcct attgcggatg ttgttgc                                            27

<210> SEQ ID NO 30
<211> LENGTH: 19
<212> TYPE: DNA
<213> ORGANISM: A. oryzae
<220> FEATURE:
<221> NAME/KEY: misc_feature
<222> LOCATION: (3)..(3)
<223> OTHER INFORMATION: y= c or t
<220> FEATURE:
<221> NAME/KEY: misc_feature
<222> LOCATION: (6)..(6)
<223> OTHER INFORMATION: n= inosine
<220> FEATURE:
<221> NAME/KEY: misc_feature
<222> LOCATION: (9)..(9)
<223> OTHER INFORMATION: y= c or t
<220> FEATURE:
<221> NAME/KEY: misc_feature
<222> LOCATION: (15)..(15)
<223> OTHER INFORMATION: y= c or t
<220> FEATURE:
<221> NAME/KEY: misc_feature
<222> LOCATION: (18)..(18)
<223> OTHER INFORMATION: n= a,c,g or t

<400> SEQUENCE: 30
gayccngayt ggaayccng                                                     19

<210> SEQ ID NO 31
<211> LENGTH: 20
<212> TYPE: DNA
<213> ORGANISM: A. oryzae
<220> FEATURE:
<221> NAME/KEY: misc_feature
<222> LOCATION: (3)..(3)
<223> OTHER INFORMATION: y= c or t
<220> FEATURE:
<221> NAME/KEY: misc_feature
<222> LOCATION: (6)..(6)
<223> OTHER INFORMATION: y= c or t
<220> FEATURE:
<221> NAME/KEY: misc_feature
<222> LOCATION: (9)..(9)
<223> OTHER INFORMATION: n= inosine
<220> FEATURE:
<221> NAME/KEY: misc_feature
<222> LOCATION: (12)..(12)
<223> OTHER INFORMATION: r= a or g
<220> FEATURE:
<221> NAME/KEY: misc_feature
<222> LOCATION: (15)..(15)
<223> OTHER INFORMATION: n= a,c,g, or t
<220> FEATURE:
<221> NAME/KEY: misc_feature
<222> LOCATION: (17)..(17)
<223> OTHER INFORMATION: k= g or t
```

```
<400> SEQUENCE: 31
ttyttytgnc crtcnckcca                                              20

<210> SEQ ID NO 32
<211> LENGTH: 20
<212> TYPE: DNA
<213> ORGANISM: A. oryzae
<220> FEATURE:
<221> NAME/KEY: misc_feature
<222> LOCATION: (3)..(3)
<223> OTHER INFORMATION: y= c or t
<220> FEATURE:
<221> NAME/KEY: misc_feature
<222> LOCATION: (6)..(6)
<223> OTHER INFORMATION: y= c or t
<220> FEATURE:
<221> NAME/KEY: misc_feature
<222> LOCATION: (9)..(9)
<223> OTHER INFORMATION: n= inosine
<220> FEATURE:
<221> NAME/KEY: misc_feature
<222> LOCATION: (12)..(12)
<223> OTHER INFORMATION: r= a or g
<220> FEATURE:
<221> NAME/KEY: misc_feature
<222> LOCATION: (15)..(15)
<223> OTHER INFORMATION: n= a,c,g, or t
<220> FEATURE:
<221> NAME/KEY: misc_feature
<222> LOCATION: (16)..(16)
<223> OTHER INFORMATION: y= c or t
<220> FEATURE:
<221> NAME/KEY: misc_feature
<222> LOCATION: (18)..(18)
<223> OTHER INFORMATION: n= a,c,g, or t

<400> SEQUENCE: 32
aaytayacnc aracnytnga                                              20

<210> SEQ ID NO 33
<211> LENGTH: 19
<212> TYPE: DNA
<213> ORGANISM: A. oryzae
<220> FEATURE:
<221> NAME/KEY: misc_feature
<222> LOCATION: (3)..(3)
<223> OTHER INFORMATION: n= inosine
<220> FEATURE:
<221> NAME/KEY: misc_feature
<222> LOCATION: (6)..(6)
<223> OTHER INFORMATION: y= c or t
<220> FEATURE:
<221> NAME/KEY: misc_feature
<222> LOCATION: (9)..(9)
<223> OTHER INFORMATION: y= c or t
<220> FEATURE:
<221> NAME/KEY: misc_feature
<222> LOCATION: (12)..(12)
<223> OTHER INFORMATION: d= a,g, or t
<220> FEATURE:
<221> NAME/KEY: misc_feature
<222> LOCATION: (15)..(15)
<223> OTHER INFORMATION: n= a,c,g, or t
<220> FEATURE:
<221> NAME/KEY: misc_feature
<222> LOCATION: (18)..(18)
<223> OTHER INFORMATION: n= a,c,g, or t

<400> SEQUENCE: 33
atnttytcyt cdatngtnc                                               19
```

```
<210> SEQ ID NO 34
<211> LENGTH: 19
<212> TYPE: DNA
<213> ORGANISM: A. oryzae

<400> SEQUENCE: 34
aatgcttgtt gatcagcag                                              19
```